United States Patent
Canady et al.

(10) Patent No.: US 11,167,146 B2
(45) Date of Patent: Nov. 9, 2021

(54) SYSTEM FOR TREATMENT OF RESPIRATORY INFECTIONS AND CANCERS OF THE RESPIRATORY SYSTEM USING COLD ATMOSPHERIC PLASMA

(71) Applicant: Jerome Canady Research Institute for Advanced Biological and Technological Sciences, Takoma Park, MD (US)

(72) Inventors: Jerome Canady, Lakeland, FL (US); Taisen Zhuang, Rockville, MD (US); Xiaoqian Cheng, Falls Church, VA (US); Evgueni Sokolovski, Herdon, VA (US); Saravana Murthy, Owings Mills, MD (US); Buddika Sumanasena, Silver Spring, MD (US); Feng Yan, Fairfax, VA (US); Cheffran Canady, Erie, CO (US); Jerome McQueen, Annandale, VA (US)

(73) Assignee: Jerome Canady Research Institute for Advanced Biological and Technological Sciences, Takoma Park, MD (US)

( * ) Notice: Subject to any disclaimer, the term of this patent is extended or adjusted under 35 U.S.C. 154(b) by 0 days.

(21) Appl. No.: 17/284,762

(22) PCT Filed: Dec. 30, 2020

(86) PCT No.: PCT/US2020/067503
§ 371 (c)(1),
(2) Date: Apr. 12, 2021

(65) Prior Publication Data
US 2021/0316153 A1 Oct. 14, 2021

Related U.S. Application Data

(60) Provisional application No. 63/033,561, filed on Jun. 2, 2020, provisional application No. 63/014,657, filed
(Continued)

(51) Int. Cl.
*A61N 1/44* (2006.01)
*A61K 33/00* (2006.01)
(Continued)

(52) U.S. Cl.
CPC ........... *A61N 1/44* (2013.01); *A61K 33/00* (2013.01); *A61M 16/022* (2017.08);
(Continued)

(58) Field of Classification Search
CPC ........... A61M 16/00; A61M 16/0003; A61M 16/0057; A61M 16/0066; A61M 16/022;
(Continued)

(56) References Cited

U.S. PATENT DOCUMENTS 6,013,153 A * 1/2000 Koinuma ............ B29C 59/106
156/272.6
6,037,274 A * 3/2000 Kudo .................. C23C 16/401
438/778
(Continued)

FOREIGN PATENT DOCUMENTS

EP 2682063 A1 1/2014
WO 2018189174 A1 10/2018
(Continued)

OTHER PUBLICATIONS

Keidar M, Beilis II, "Plasma Engineering: application in aerospace, nanotechnology and bionanotechnology," Oxford: Elsevier; 2013.
(Continued)

*Primary Examiner* — Joseph D. Boecker
(74) *Attorney, Agent, or Firm* — 24IP Law Group USA, PLLC; Timothy DeWitt

(57) ABSTRACT

A system for performing cold atmospheric plasma treatment of respiratory infections or lung cancer having a source of a carrier gas, a cold atmospheric plasma generator connected to the source of carrier gas, a source of compressed air, a humidifier connected to the source of compressed air, a source of oxygen, a ventilator having inputs connected to an output of the humidifier and the source of oxygen, a mixer having an interior chamber formed from a dielectric, an active electrode inside the interior chamber, and an outer electrode connected to ground, wherein the mixer has a fluid input port connected to a gas output of the cold atmospheric plasma generator and an output of the ventilator, and a delivery member connected to an output of the mixer for delivering combined humidified air and cold atmospheric plasma to a respiratory system of a patient.

19 Claims, 38 Drawing Sheets

Related U.S. Application Data on Apr. 23, 2020, provisional application No. 63/010,565, filed on Apr. 15, 2020, provisional application No. 63/008,510, filed on Apr. 10, 2020.

(51) Int. Cl.

| *A61M 16/16* | (2006.01) |
| *A61M 16/06* | (2006.01) |
| *A61M 16/10* | (2006.01) |
| *A61M 16/12* | (2006.01) |
| *A61M 16/00* | (2006.01) |

(52) U.S. Cl.
CPC .... *A61M 16/0666* (2013.01); *A61M 16/0672* (2014.02); *A61M 16/1005* (2014.02); *A61M 16/12* (2013.01); *A61M 16/16* (2013.01); *A61M 2202/025* (2013.01)

(58) Field of Classification Search
CPC .. A61M 16/10; A61M 16/1005; A61M 16/12; A61M 16/16; A61M 11/00; A61M 13/003; A61M 15/00; A61M 15/02; A61M 2202/025; A61N 1/44; A61B 18/042; A61B 18/1206; A61B 18/00583
See application file for complete search history.

(56) References Cited

U.S. PATENT DOCUMENTS

| 6,786,217 | B2 | 7/2004 | Stenzler |
| 8,460,283 | B1 | 6/2013 | Laroussi et al. |
| 8,554,298 | B2 | 10/2013 | Doyle et al. |
| 9,999,462 | B2 | 6/2018 | Canady et al. |
| 10,213,614 | B2 | 2/2019 | Guron et al. |
| 10,350,374 | B2 | 7/2019 | Robinson et al. |
| 10,479,979 | B2 | 11/2019 | Canady et al. |
| 2001/0051228 | A1* | 12/2001 | Sugahara ............... C23C 16/401 427/489 |
| 2004/0000476 | A1 | 1/2004 | Cho et al. |
| 2010/0130973 | A1* | 5/2010 | Choi ..................... A61B 18/042 606/40 |
| 2011/0071517 | A1* | 3/2011 | Konesky .............. A61B 18/042 606/40 |
| 2011/0101862 | A1* | 5/2011 | Koo .................. H01J 37/32449 315/111.21 |
| 2012/0064016 | A1* | 3/2012 | Lloyd .................. A61B 18/042 424/49 |
| 2012/0259272 | A1* | 10/2012 | Staack ...................... A61L 2/14 604/24 |
| 2013/0068226 | A1 | 3/2013 | Watson et al. |
| 2013/0074838 | A1 | 3/2013 | Bathe et al. |
| 2013/0092159 | A1 | 4/2013 | Koebrich et al. |
| 2014/0224643 | A1* | 8/2014 | Collins ............... H01J 37/3255 204/164 |
| 2014/0276784 | A1 | 9/2014 | Ward et al. |
| 2015/0034082 | A1 | 2/2015 | Jafari et al. |
| 2015/0038790 | A1 | 2/2015 | Rontal et al. |
| 2015/0059743 | A1 | 3/2015 | Aikawa et al. |
| 2015/0279629 | A1* | 10/2015 | Liao .................. H01J 37/32981 315/111.21 |
| 2017/0164873 | A1 | 6/2017 | Lee et al. |
| 2018/0271582 | A1* | 9/2018 | Canady .................... H05H 1/46 |
| 2019/0279849 | A1 | 9/2019 | Canady et al. |
| 2020/0016286 | A1 | 1/2020 | Clack et al. |

FOREIGN PATENT DOCUMENTS

| WO | 2018191265 A1 | 10/2018 |
| WO | 2019199281 A1 | 10/2019 |

OTHER PUBLICATIONS

Chauvin, J., Judée, F., Yousfi, M. et al., "Analysis of reactive oxygen and nitrogen species generated in three liquid media by low temperature helium plasma jet," Sci Rep 7, 4562 (2017).

M. Keidar, et al., "Cold plasma selectivity and the possibility of a paradigm shift in cancer therapy," British Journal of Cancer (2011) 105(9), 1295-1301.

Yan D, Sherman J H and Keidar M, "Cold atmospheric plasma, a novel promising anticancer treatment modality," Oncotarget. 8 15977-15995 (2017).

Keidar M, "Plasma for cancer treatment," Plasma Sources Sci. Technol. 24 33001 (2015).

Hirst A M, Frame F M, Arya M, Maitland N J and O'Connell D, "Low temperature plasmas as emerging cancer therapeutics: the state of play and thoughts for the future," Tumor Biol. 37 7021-7031 (2016).

t. Xie, et al., "Inactivation of airborne viruses using a packed bed non-thermal plasma reactor," J. Phys. Appl. Phys. 52 (2019).

Chernets N, Kurpad D S, Alexeev V,Rodrigues D B and Freeman T A, "Reaction chemistry generated by nanosecond pulsed dielectric barrier discharge treatment is responsible for the tumor eradication in the B16 melanoma mouse model," Plasma Process. Polym. 12 1400-1409 (2015).

J. Zimmerman, et al., "Effects of cold atmospheric plasmas on adenoviruses in solution," J. Phys., D: 44 (2011) 505201.

X. Su et al., "Inactivation Efficacy of Nonthermal Plasma-Activated Solutions Against Newcastle Disease Virus," Applied and Environmental Microbiology, May 2018, vol. 84, issue 9.

\* cited by examiner

SYSTEM FOR TREATMENT OF RESPIRATORY INFECTIONS AND CANCERS OF THE RESPIRATORY SYSTEM USING COLD ATMOSPHERIC PLASMA

CROSS-REFERENCE TO RELATED APPLICATIONS

The present application claims the benefit of the filing date of U.S. Provisional Patent Application Ser. No. 63/008,510 filed on Apr. 10, 2020, U.S. Provisional Patent Application Ser. No. 63/010,565 filed on Apr. 15, 2020, and U.S. Provisional Patent Application Ser. No. 63/014,657 filed on Apr. 23, 2020, and U.S. Provisional Patent Application Ser. No. 63/033,561 filed on Jun. 2, 2020.

The aforementioned provisional patent applications are hereby incorporated by reference in their entirety.

STATEMENT REGARDING FEDERALLY SPONSORED RESEARCH OR DEVELOPMENT

None.

BACKGROUND OF THE INVENTION

Field of the Invention

The present invention relates to systems and methods for using cold atmospheric plasma to treat respiratory infections, lung cancer, pneumonia, or other cancers of the respiratory system.

Brief Description of the Related Art

Plasma medicine has qualified as a new scientific field after intense research effort in low-temperature or cold atmospheric plasma applications. Keidar M, Beilis II, "Plasma Engineering: application in aerospace, nanotechnology and bionanotechnology," Oxford: Elsevier; 2013. It is known that cold atmospheric plasmas ("CAP") produce various chemically reactive species including reactive oxygen species (ROS) and reactive nitrogen species (RNS). Chauvin, J., Judée, F., Yonsfi, M. et al., "Analysis of reactive oxygen and nitrogen species generated in three liquid media by low temperature helium plasma jet," *Sci Rep* 7, 4562 (2017). CAP is a cocktail containing ROS and RNS in combination with transient electric fields, UV and charged species.

CAP has already been proven to be effective in wound healing, skin diseases, hospital hygiene, sterilization, antifungal treatments, dental care, and cosmetics targeted cell/tissue removal. One of the most recent applications of CAP is in cancer therapy. M. Keidar, et al., "Cold plasma selectivity and the possibility of a paradigm shift in cancer therapy," British Journal of Cancer (2011) 105(9), 1295-1301. As a near-room temperature ionized gas, cold atmospheric plasma (CAP) has demonstrated its promising capability in cancer treatment by causing the selective death of cancer cells in vitro. See, Yan D, Sherman J H and Keidar M, "Cold atmospheric plasma, a novel promising anti-cancer treatment modality," *Oncotarget.* 8 15977-15995 (2017); Keidar M, "Plasma for cancer treatment," *Plasma Sources Sci. Technol.* 24 33001 (2015); Hirst A M, Frame F M, Arya M, Maitland N J and O'Connell D, "Low temperature plasmas as emerging cancer therapeutics: the state of play and thoughts for the future," *Tumor Biol.* 37 7021-7031 (2016). The CAP treatment on several subcutaneous xenograft tumors and melanoma in mice has also demonstrated its potential clinical application. See, Keidar M, Walk R, Shashurin A, Srinivasan P, Sandler A, Dasgupta S, Ravi R, Guerrero-Preston R and Trink B, "Cold plasma selectivity and the possibility of a paradigm shift in cancer therapy," *Br. J. Cancer.* 105 1295-301 (2011); Chernets N, Kurpad D S, Alexeev V, Rodrigues D B and Freeman T A, "Reaction chemistry generated by nanosecond pulsed dielectric barrier discharge treatment is responsible for the tumor eradication in the B16 melanoma mouse model," *Plasma Process. Polym.* 12 1400-1409 (2015).

Additionally, various experiments have been performed in connection with the effect of CAP on viruses. In J. Zimmerman, et al., "Effects of cold atmospheric plasmas on adenoviruses in solution," J. Phys., D: 44 (2011) 505201, the authors reported successful inactivation of adenovirus, a non-enveloped double stranded DNA virus, in a solution using a surface micro-discharge technology operating in air. In X. Su et al., "Inactivation Efficacy of Nonthermal Plasma-Activated Solutions Against Newcastle Disease Virus," Applied and Environmental Microbiology, May 2018, vol. 84, issue 9, the authors reported on their investigation of the inactivation efficacy of Newcastle disease virus by non-thermal plasma-activated solutions. In T. Xie, et al., "Inactivation of airborne viruses using a packed bed non-thermal plasma reactor," J. Phys. Appl. Phys. 52 (2019), the authors reported on their study of the effectiveness of a packed bed dielectric barrier discharge (DBD) NTP reactor to inactivate bacteriophage MS2 in aerosols. See also, U.S. Published Patent Application No. 2020/0016286, entitled "Production of Immune-response Stimulating Aerosols by Non-thermal Plasma Treatment of Airborne Pathogens."

Several different systems and methods for performing Cold Atmospheric Plasma (CAP) treatment have been disclosed. For example, U.S. Pat. No. 10,213,614 discloses a two-electrode system for CAP treatement of cancer cells.

Another exemplary Cold Atmospheric Plasma system is disclosed in U.S. Pat. No. 9,999,462. The disclosed system has two units, namely a Conversion Unit (CU) and a Cold Plasma Probe (CPP). The Conversion Unit is connected to high frequency electrosurgical generator (ESU) output and converts the ESU signal to a signal appropriate for performing cold atmospheric plasma procedures. The Cold Plasma Probe is connected to the Conversion Unit output. At the end of the Cold Plasma Probe cold plasma is produced and is thermally harmless to living tissue, i.e., it cannot cause burns to the tissue. This cold plasma, however, is deadly for cancer cells while leaving normal cells unaffected. The disclosed Cold Plasma Conversion Unit is unique in that it utilizes a high voltage transformer to up-convert the voltage (1.5-50 kV), down-convert the frequency (<300 kHz), and down-convert the power (<30 W) of the high-voltage output from an electrosurgical unit (U.S. Pat. No. 9,999,462).

Additional research has shown that these CAP systems can be used to stimulate media, which then can be used for cancer treatment. For example, U.S. Pat. No. 10,479,979, discloses a method for preparing a CAP stimulated media for use in cancer treatment. Another method for preparing CAP stimulated media is disclosed in U.S. Published Patent Application No. 2019/0279849.

Further, various systems and methods for controlling gas flow and an integrated gas-assisted electrosurgical generator having a graphical user interface is disclosed in WO2018/191265, entitled "Electrosurgical Gas Control Module" and WO2019199281, entitled "Gas Enhanced Electrosurgical Generator."

A variety of medical ventilator systems have been disclosed. Medical ventilators typically have a source of pressurized oxygen, which is fluidly connected to a patient through a conduit. For example, U.S. Pat. No. 10,350,374 discloses a medical system having a ventilator coupled to a breaching circuit. Some ventilator systems add means for monitoring patient data. For example, U.S. Pat. No. 8,554,298 discloses systems and methods for managing ventilation of a patient being ventilated by a medical ventilator, and in particular, for integrating oximeter data with the medical ventilator. Another example is U.S. Published Patent Application No. 20150034082, which discloses a ventilator-extracorporeal membrane gas-exchange (ECGE) system. Yet another example is U.S. Published Patent Application No. 20170164873, which discloses a medical ventilator with a pneumonia and pneumonia bacterial disease analysis function by using gas recognition.

Still other systems include means for supplying a medical gas with a ventilator. U.S. Published Patent Application No. 2013/0092159 discloses a method and device for supplying at least one medical gas to a patient receiving artificial respiration with the aid of a ventilator. A gas mixture provided by a respiratory gas flow of a ventilator and a medical gas added to the flow are supplied to a connecting piece, such as a Y-piece or Y-connector from which a patient feed line leads to the mechanically ventilated patient and from which a further line branches off. Via this further line at least the gas exhaled by the patient and the proportion of the respiratory gas introduced to the first line by the ventilator and the medical gas fed into the first line which have not been inhaled by the patient are discharged via the second line. For example, U.S. Published Patent Application No. 20150059743 discloses a ventilator for supplying a mixed gas of oxygen and a medical gas other than oxygen to a patient.

SUMMARY OF THE INVENTION

In a preferred embodiment, the present invention is a system and method for using cold atmospheric plasma to treat respiratory infections or cancers of the respiratory system, and, in particular, to treat patients having COVID-19.

In a preferred embodiment, the present invention is a system for performing plasma treatment of respiratory infections. "Plasma treatment of respiratory infections" as used herein refers to the use of a plasma to generate reactive species to be delivered to a patient's respiratory system. The system has a source of a carrier gas, a humidifier connected to the source of a carrier gas, a source of a feed gas, a humidifier connected to the source of a feed gas, a plasma generator configured to plasmatize the carrier gas into a plasma, a mixer and a fluid delivery member connected to an output of the mixer for delivering reactive species generated in the mixer to a patient. The mixer has an interior chamber formed from a dielectric, an active electrode inside the interior chamber and connected to an electrical output of the plasma generator, and an outer electrode connected to a ground, wherein the mixer has a first fluid input port connected to the source of a carrier gas and a second fluid input connected to the source of a feed gas. The structure of the mixer forms a dielectric barrier discharge system for generating plasma. The carrier gas may comprise at least one of helium, argon, nitrogen and oxygen. The delivery member, for example, may be endobronchial tube, a nasal cannula or a face mask. The source of a feed gas comprises one of a ventilator and a continuous positive airway pressure device and may comprise a mixture of air and oxygen.

The plasma generator preferably operates with a frequency in the range of 10 kHz to 200 kHz and an output peak voltage in the range of 3 kV to 6 kV. In a preferred embodiment, the plasma generator generates electrical energy having a frequency within 5 kHz of one of 40 kHz, 100 kHz and 200 kHz. In another preferred embodiment, the plasma generator generates electrical energy having a frequency of 122 kHz. The plasma generator may be a combination a high frequency electrosurgical generator and a low frequency converter. The plasma generator may have a power module, a CPU for controlling the power module, a memory connected to the CPU and a power supply connected to the CPU. Still further, the plasma generator may have a touchscreen display, a controller connected to the touchscreen display and a graphical user interface configured to display data on the touchscreen display and receive input from a user through the touch-screen display. The plasma generator further may have a gas module. The source of a carrier gas may be connected to the gas module and the gas module controls a flow of the carrier gas to the mixer. The first humidifier may be connected between the gas module and the mixer or may be connected between the gas module and the source of a carrier gas.

In a preferred embodiment, the first humidifier is configured to humidify a carrier gas flowing from the source of a carrier gas to at least 70% humidity and the second humidifier is configured to humidify a feed gas flowing from the source of a feed gas to at least 50% humidity. For example, the first humidifier is configured to humidify a carrier gas flowing from the source of a carrier gas to 100% humidity and the second humidifier is configured to humidify a feed gas flowing from the source of a feed gas to at least 50% humidity.

In another embodiment, the present invention is a system for performing plasma treatment of respiratory system. The system has an electrical energy generator configured to generate electrical energy to plasmatize a carrier gas into a plasma and a dielectric barrier discharge ("DBD") mixer. The DBD mixer has an interior chamber formed from a dielectric, the interior chamber having a first input configured to fluidly connect to a source of a humidified carrier gas, a second input configured to connect to a source of a humidified feed gas, and an output configured to connect to a delivery member, an active electrode inside the interior chamber and connected to an electrical output of the electrical energy generator, and an outer electrode connected to a ground. A plasma is generated in the interior chamber when electrical energy is supplied from the electrical energy generator to the interior electrode while both humidified feed gas and humidified carrier gas flow into the interior chamber. The system further may have a first humidifier fluidly connected to the first input of the chamber in the dielectric barrier discharge assembly and a second humidifier fluidly connected to the second input of the chamber in the dielectric barrier discharge assembly. Still further, the system may have a source of un-humidified helium fluidly connected to an input of the first humidifier and a source of un-humidified air fluidly connected to an input of the second humidifier.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which:

FIG. 2I is a right side view of a preferred embodiment of a CAP joint mixer or dielectric barrier discharge (DBD) assembly in accordance with the preferred embodiments of the present invention.

DETAILED DESCRIPTION OF THE PREFERRED EMBODIMENTS

Figure 1A:
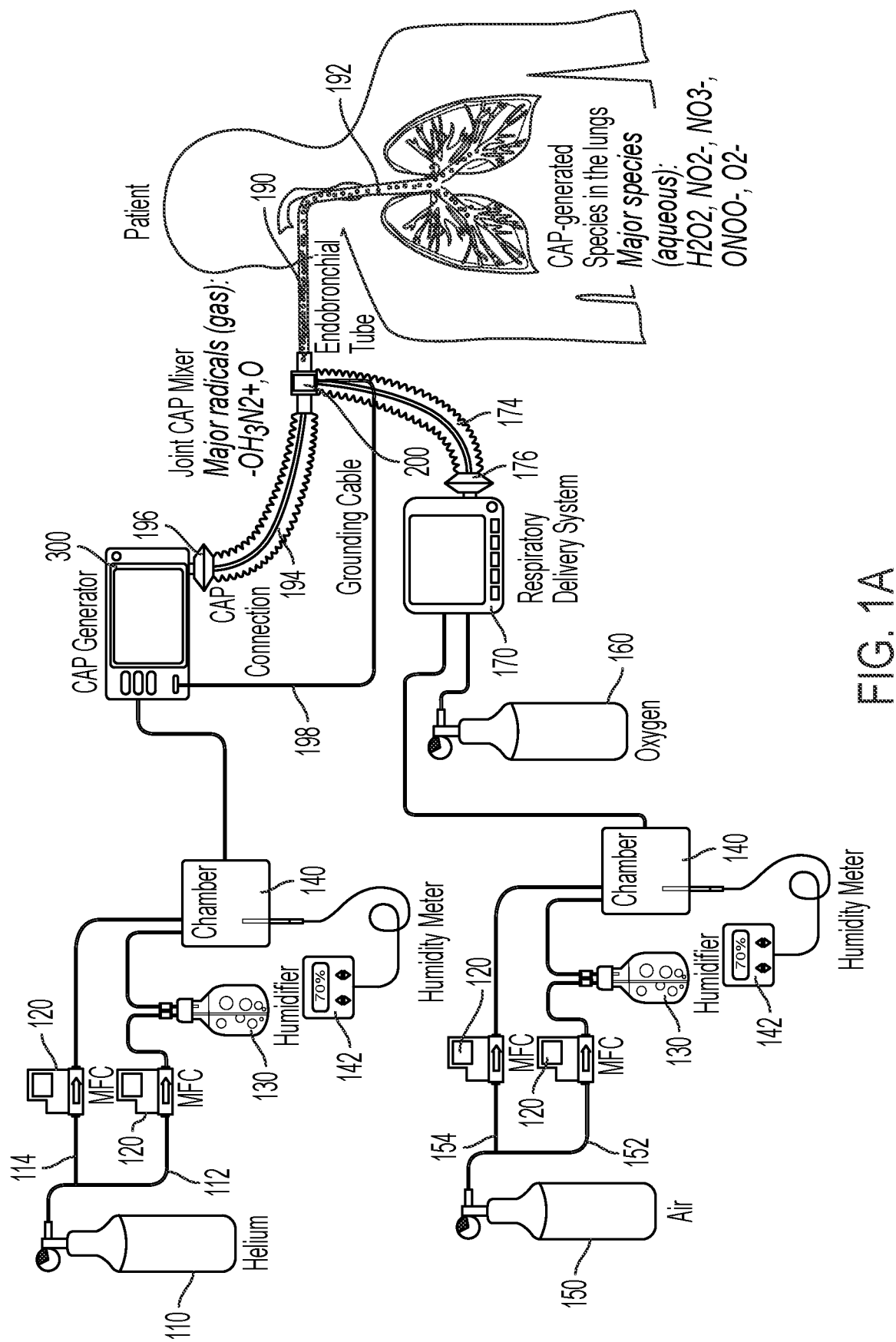
FIG. 1A is a block diagram of a cold atmospheric plasma system having a CAP Joint Mixer for treatment of respiratory infections in accordance with a preferred embodiment in which both a carrier gas and a feed gas are humidified.
Figure 1B:
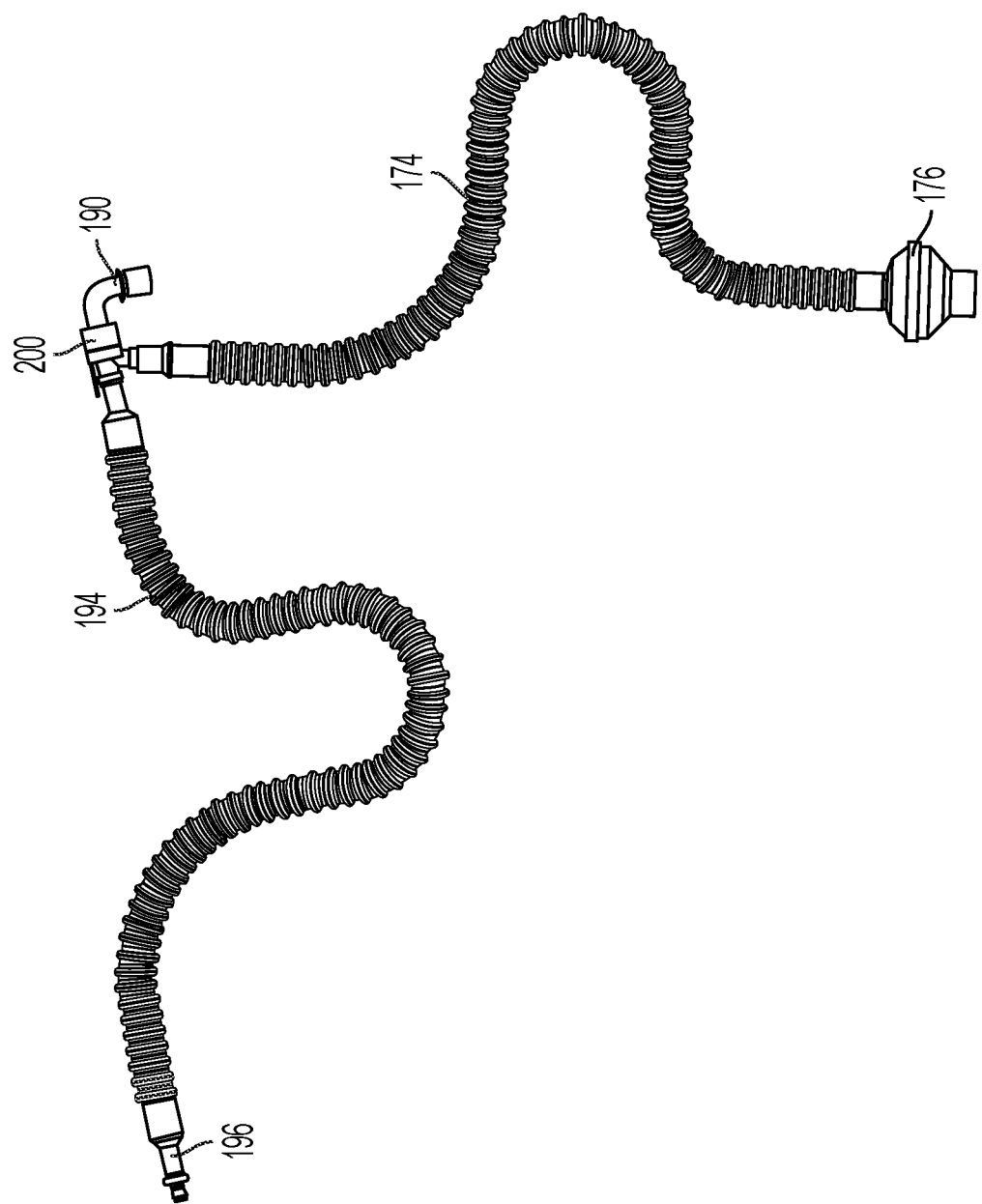
FIG. 1B is an illustration of a system layout for the dielectric barrier discharge assembly and connecting hoses of FIG. 1A.
Figure 1C:
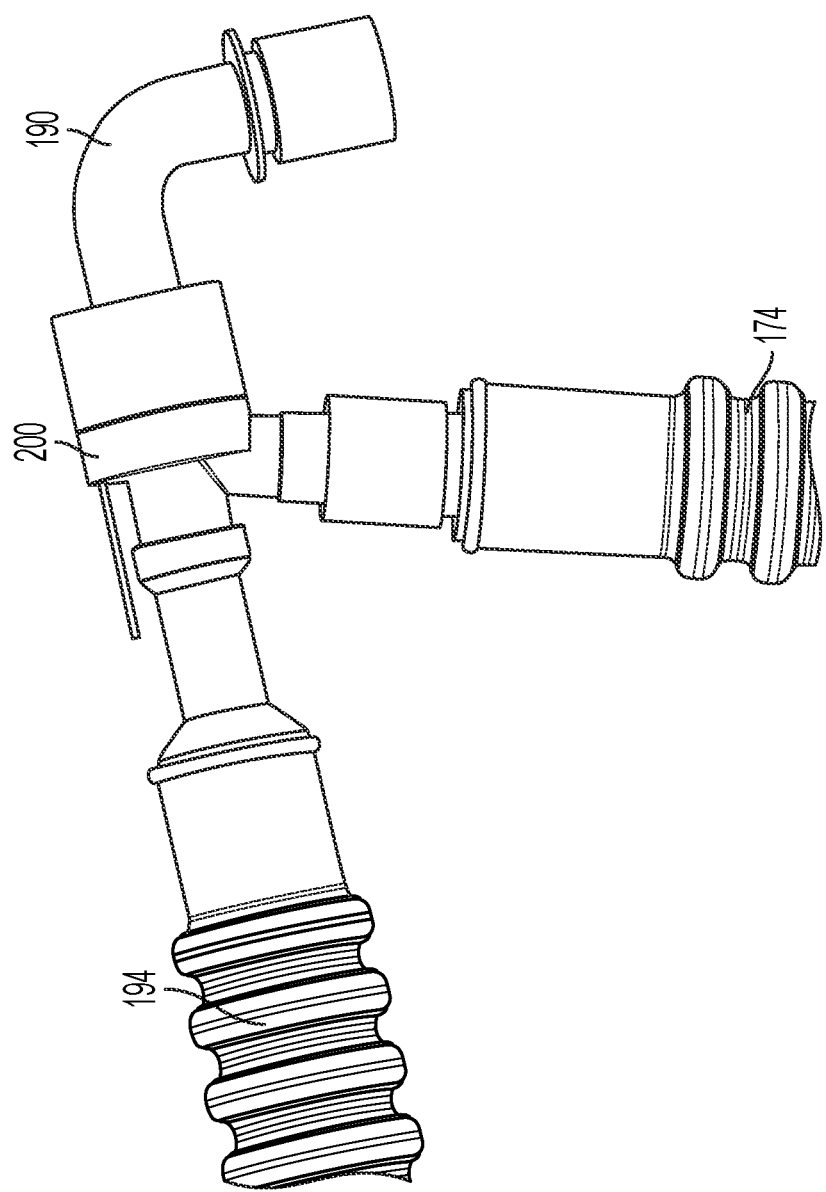
FIG. 1C is a close-up view of a system layout for the dielectric barrier discharge assembly and connecting hoses of FIG. 1A.
Figure 1D:
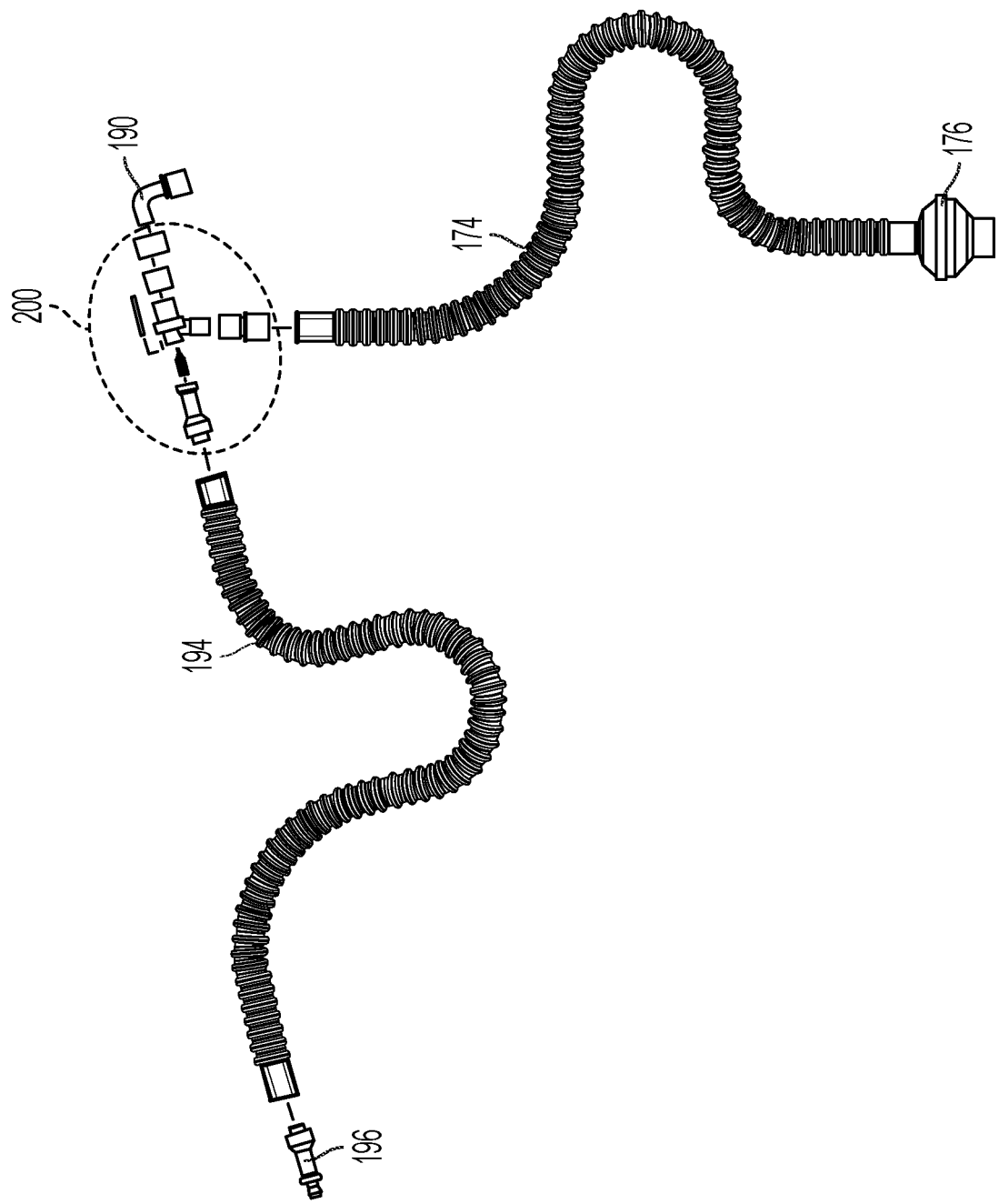
FIG. 1D is an exploded view of a system layout for the dielectric barrier discharge assembly and connecting hoses of FIG. 1A.
Figure 1E:
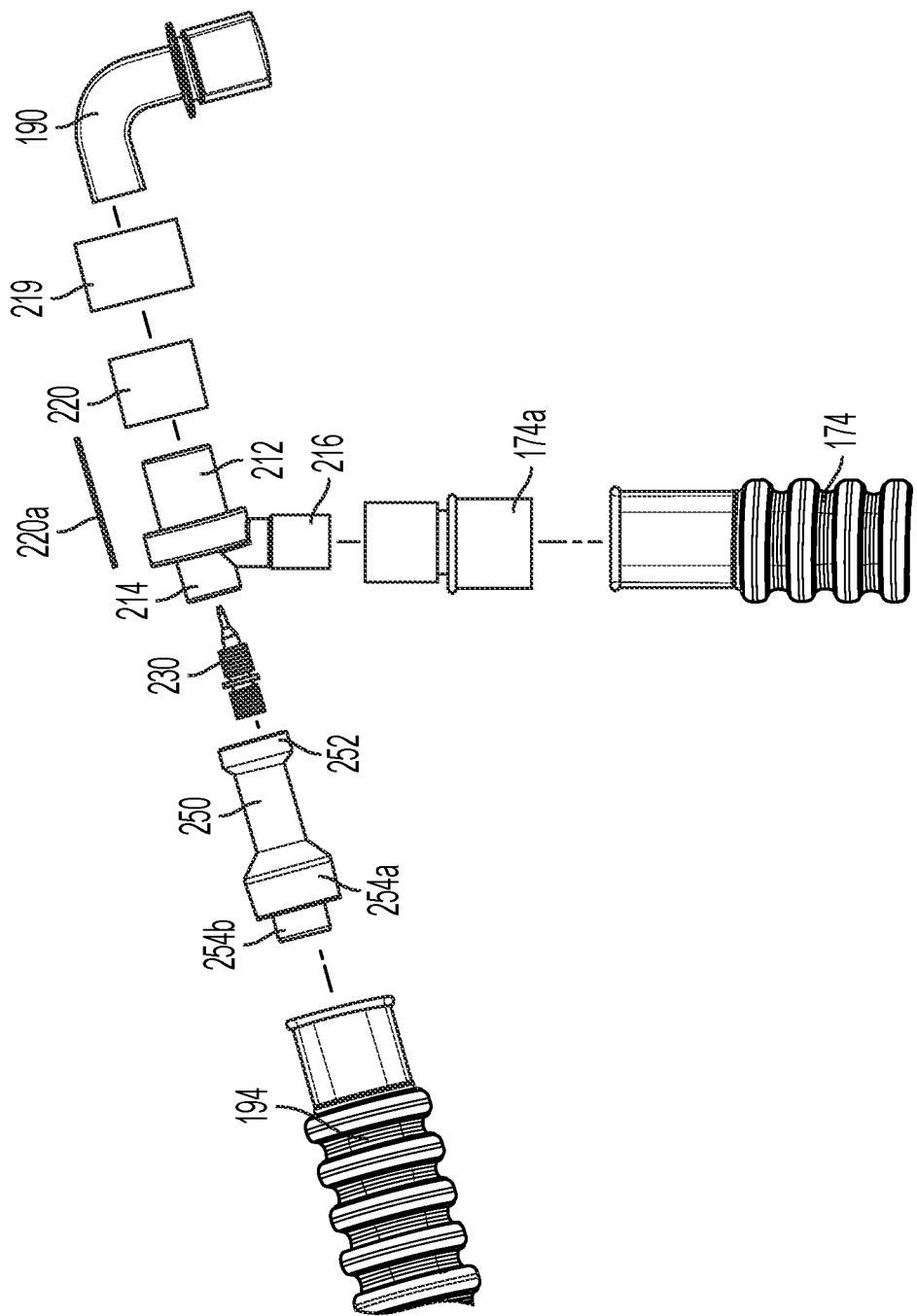
FIG. 1E is a close-up exploded view of a system layout for the dielectric barrier discharge assembly and connecting hoses of FIG. 1A.
Figure 1F:
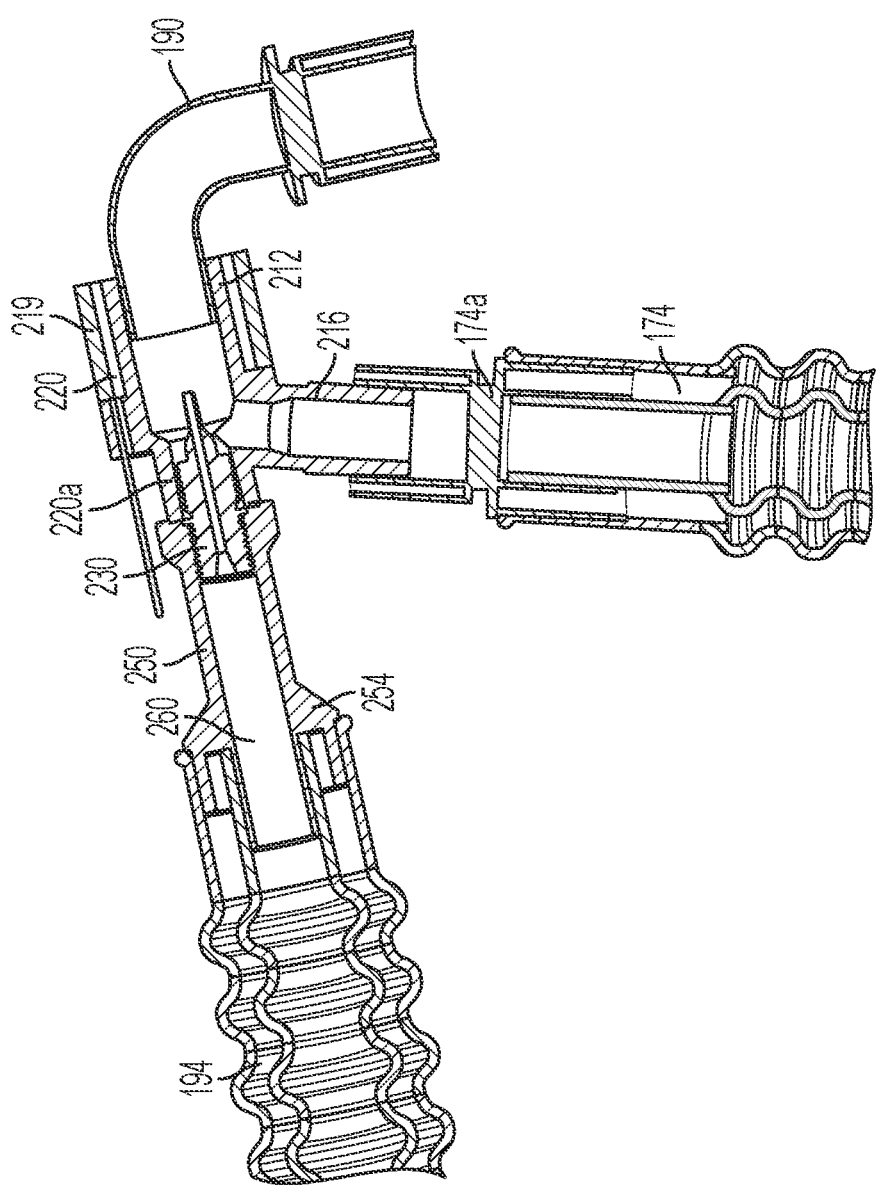
FIG. 1F is a close-up cross-sectional view of a system layout for the dielectric barrier discharge assembly and connecting hoses of FIG. 1A.

Cold atmospheric-pressure plasma (CAP) generates numerous reactive oxygen species (ROS) and reactive nitrogen species (RNS), such as hydroxyl radical (.OH), singlet oxygen ($^1O_2$), nitrogen ion ($N_2^+$), atomic oxygen (O), and, as well as electrons, ions, and photons. Maximum concentration of these species can be reached with optimal amount of humidity in the gas. CAP-generated ROS and RNS can form hydrogen peroxide ($H_2O_2$), nitrite ($NO_2$), nitrate ($NO_3^-$), peroxynitrite (ONOO—) when interacting with biological fluid. Reactive species and radicals in the plasma phase (.OH, $N_2^+$, $^1O_2$, O) are short-lived species, whereas $H_2O_2$, $NO_2^-$, $NO_3^-$, and ONOO— in aqueous phase are long-lived species. The long-lived species will further interact with intracellular species and metabolic pathways, inducing cell apoptosis. The present invention provides a system and method with which a cold atmospheric plasma (non-thermal plasma) can be generated and the reactive species can be delivered to patients across much greater distances than in prior systems. While prior systems typically are used at a distance of 2-10 cm from the target tissue, the present invention delivers plasma to the patient from a distance of greater than 10 cm.

A cold atmospheric plasma system for treatment of respiratory infections in accordance with a first preferred embodiment of the present invention is described with reference to FIG. 1. In this embodiment, the carrier as is helium and the feed gas is air. A helium gas source 110 is split into two lines 112, 114, with each of the two lines controlled by a mass flow controller (MFC) 120. Line 112 is fluidly connected to a first Humidifier 130. The Helium gas flow (50 to 1000 mL/min) in line 112 is passed through an $H_2O$ filled container (Humidifier 130) and then fed into a mixing chamber 140. The helium gas flow in the line 114 is fed directly into the mixing chamber 140. In this manner, with the mass flow controllers 120 on the lines 112, 114 a relative $H_2O$ saturation in the gas exiting the chamber 140 can be adjusted. Adjustment of the gas flow in the two lines 112, 114 makes the overall flow rate and humidity fine tuning of the gas flow exiting the chamber 140 possible. The humidity may be in the range of 20%-100% with a preferred humidity of at least 70%. The total helium flow in this embodiment could be varied from 0.5 L/min to 5 L/min in all cases. The humidity of Helium gas in the chamber 140 is measured via calibrated High-Accuracy Humidity and Temperature Meter 142. The humidified helium gas from the chamber 140 is fed into an electrosurgical generator 300, referred to herein as a "Cold Atmospheric Plasma (CAP) Generator." A variety of electrosurgical generators are known in the art and could be used with the present invention. The gas being fed into the Cold Atmospheric Plasma (CAP) Generator 300 is referred to herein as the "carrier gas."

At the same time, an un-humidified air supply 150 (feed gas) is split into two lines 152, 154. Each line 152, 154 is controlled by a mass flow controllers (MFC) 120. Line 152 is fluidly connected to a second Humidifier 130. The air gas flow in line 152 is passed through an $H_2O$ filled container (Humidifier 130) and then is fed into a mixing chamber 140. The air gas flow in the line 114 is fed directly into the mixing chamber 140. In this manner, with the mass flow controllers 120 on the lines 152, 154 a relative $H_2O$ saturation in the air feed exiting the chamber 140 can be adjusted. Adjustment of the air flow in the two lines 152, 154 makes the overall flow rate and humidity fine tuning possible. The humidity may be in the range of 20%-100% with a preferred humidity of at least 70%. The humidity of air in the chamber 140 is measured via calibrated High-Accuracy Humidity and Temperature Meter 142. The humidified air from the chamber 140 and oxygen from an oxygen supply 160 are provided to a respiratory delivery system 170, such as a ventilator, CPAP machine, BIPAP machine, or other known respiratory deliver system. The respiratory delivery system 170 will mix, adjust and measure the pressure, flowrate, ratio and frequency of the patient inbreath of exhaust air, oxygen and $CO_2$. The output of the respiratory delivery system 170 is connected to the CAP joint mixer, for example, via tubing 174 and a connector 176. In testing, humidifying the helium flow to 100% humidity and the air flow to 50% humidity proved to be effective.

The output of the CAP generator 300 and the respiratory delivery system 170 are connected to a dielectric barrier discharge (DBD) assembly 200, referred to herein as a "CAP joint mixer." A ground cable 198 connects an outer electrode of the CAP joint mixer 200 to a ground in the CAP generator 300. While the grounding cable 198 is shown separate from the tubing 194 in FIG. 1, other arrangements are possible in which the ground cable 198 is combined, for example, in a harness with the tubing 194. Due to the presence of the $H_2O$, the ionization of Helium and $H_2O$ to $He^+ + e^-$ chemical reaction will happen simultaneously. The cold plasma-generated reactive species (H2O2, NO2—, NO3—, ONOO—, and O2-) are produced.

The output of the CAP joint mixer 200 is connected to a delivery member 190, which, for example, may be an endobronchial tube, oxygen CPAP (continuous positive airway pressure), BIPAP (Bilevel Positive Airway Pressure), ventilator face mask, or nasal $O_2$ cannula 190 to deliver reactive species 192, e.g., H2O2, NO2—, NO3—, ONOO—, and O2-, generated by the system into the patient's respiratory system.

A preferred embodiment of a dielectric barrier discharge (DBD assembly or CAP Joint Mixer 200 is described with reference to FIGS. 2A-2I. The DBD assembly 200 has a first entry port 202 for receiving a flow of a first gas (e.g., a carrier gas), a second entry port 204 for receiving a second gas (e.g., a feed gas), and an exit port 206 through which gases and reactive species generated in the DBD assembly exit the assembly. The assembly has a primary housing 210 having a portion 212 forming a chamber 212a within the primary housing 210. At least the portion 212 forming the chamber 212a is a dielectric material. In a preferred embodiment, the entire primary housing 210 is formed of a dielectric material, but other embodiments are possible wherein only a portion of the primary housing 210 including the portion 212 that forms the chamber 212a is formed of a dielectric material. In still other embodiments, a dielectric material separate from the primary housing 210 may surround the chamber 212a. The portion 212 of the primary housing 210 forms the exit port 206 to which a delivery member, such as an endobracheal tube or other type of tube, may be connected. The invention is not limited to any particular type of delivery member or connection between the delivery member and the exit port 206. The primary housing 210 has a first neck or connector portion 214 forming a first input port 202 for receiving a first gas, which in this embodiment is the carrier gas (e.g., helium), and a channel leading to the chamber 212a. The interior of the neck portion 214 is threaded for receiving an interior electrode 230. The primary housing 210 further has a second neck or connector 216 forming a second input port 204 for receiving a second gas, which in this embodiment is a feed gas (e.g., an air/oxygen mixture) and a channel 216a leading to the chamber 212a. A second outer electrode 220 made of a conductive material, e.g., copper, surrounds the exterior of the dielectric forming the chamber 212a. As shown in FIGS. 2A and 2B, an outer insulating layer 219 covers the outer electrode 220. The outer insulating layer 219 is not shown in FIG. 2C. As shown in FIG. 1, the outer electrode 220 is connected to a ground. The housing 210 has a lip or ridge 218 abutting the outer electrode 220. Within an upper portion of the lip or ridge 218 is a hole channel 218a, which allows for the outer electrode 220 to be connected to a ground wire 198 (see FIG. 1) via connecting wire 220a.

The inner electrode 230 is made of a conductive material and has within it a channel 240 through which the first gas (a carrier gas) flows. The electrode 230 has a neck 232 that extends into the chamber 212a. The channel 240 extends through the neck 232 such that the first gas (the carrier gas) can flow into the chamber 212a. The exterior of the electrode 230 two threaded portions 230a, 230b and a lip or ridge 234. The threaded portion 230a engages with the threaded interior of the neck 214 of the primary housing 210 to secure the inner electrode 230 into the primary housing 210. The ridge or lip 234 of the electrode 230 provides a stop when the electrode 230 is fully threaded into the neck 214.

The dielectric barrier discharge (DBD) assembly 200 further has a secondary housing 250 having a channel within it through which the first gas (the carrier gas) can flow to the channel 240 in the inner electrode 230. The secondary housing 250 has a portion 252 having interior threaded for engaging the threaded portion 230b of the electrode 230 and thereby securing the secondary housing to the electrode 230 and the primary housing 210. The secondary housing 250 has at the end of the threaded portion 252 a recess for receiving the electrode ridge or lip 234 and abutting the neck 214 of the primary housing 210. The secondary housing 250 further has a connector structure 254, 254a, 254b for connecting to a hose or other tubing 194 and connector 196 to connect the dielectric barrier discharge (DBD) assembly to the CAP generator 300. Within the secondary housing 250 is a tube 260 through which the first gas (the carrier gas) flows. Within the tube 260 is an elongated electrode or wire that is connected to a conductive connector 270 (e.g., via solder). The conductive connector 270 abuts the inner electrode 230 and thus is electrically connected to the inner electrode 230.

Figure 3A:
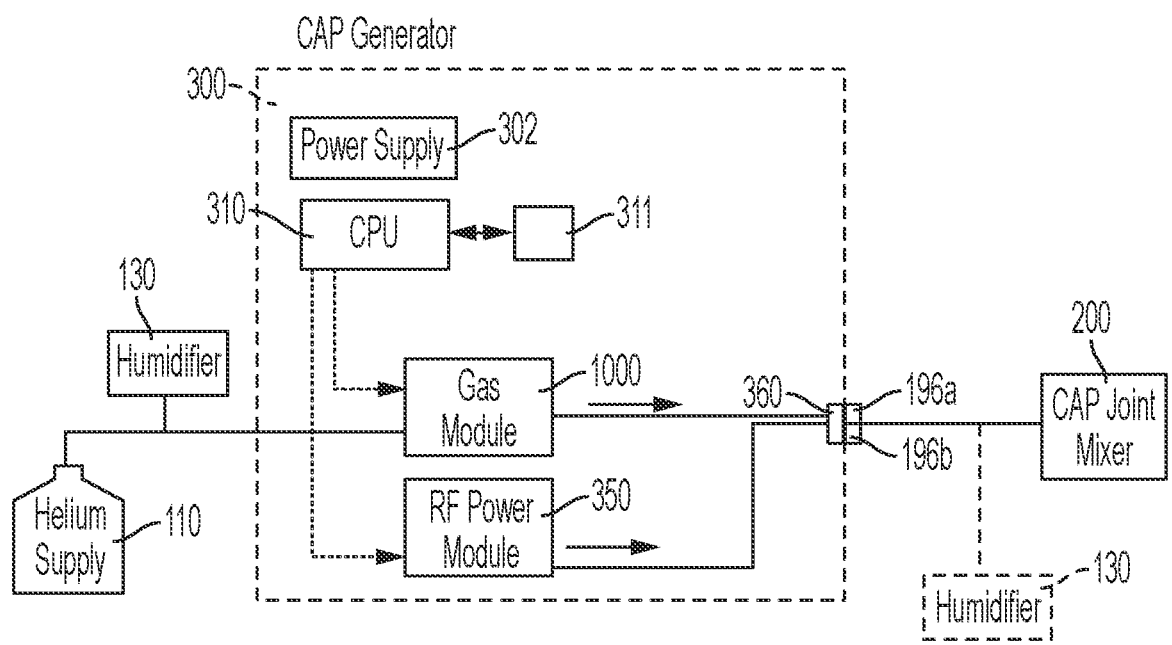
FIG. 3A is a block diagram of a cold atmospheric plasma generator of a preferred embodiment of the present invention.

As shown in FIG. 3A, an exemplary cold atmospheric plasma (CAP) generator 300 has a power supply 302, a CPU (or processor or FPGA) 310 and a memory or storage 311. The system further has a display 420 (FIG. 4), which may be the display of a tablet computer. The CPU 310 controls the system and receives input from a user through a graphical user interface displayed on display 420. The CAP generator further has a gas control module 1000 connected to a source 310 of a CAP carrier gas such as helium to control the flow of the carrier gas to the CAP joint mixer. The CAP generator 300 further has a radio frequency (RF) power module 350 for generating radio frequency (RF) energy. The RF power module contains conventional electronics such as are known for providing RF power in electrosurgical generators. The RF Power module operates with a frequency between 10-200 kHz and output peak voltage from 3 kV to 6 kV and preferably at a frequency near (within 25%) of 40 kHz, 100 kHz or 200 kHz. The gas module 1000 and RF power module 350 are connected to connector 360 that allows for CAP joint mixer 200 (or a CAP applicator 1100 in FIGS. 11A and 11B) to be connected to the generator 300 via a connector having an electrical connector 196a and gas connector 196b.

Figure 3B:
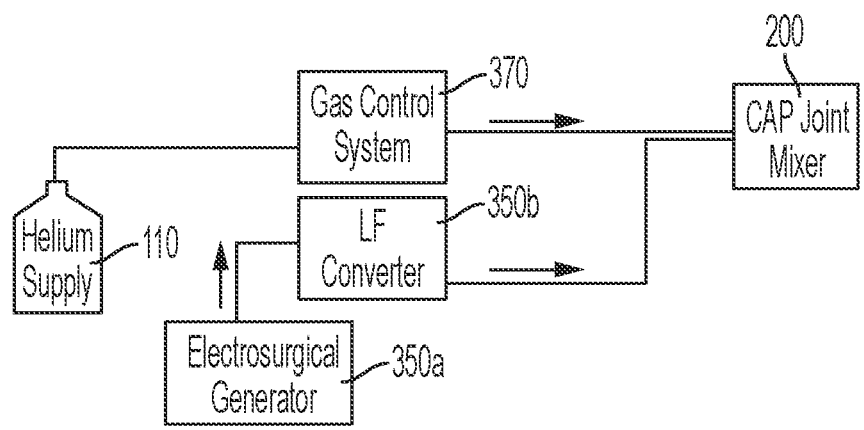
FIG. 3B is a block diagram of a plasma generator of an alternate preferred embodiment of the present invention.

As shown in FIG. 3B, other arrangements for delivery of the carrier gas and the electrical energy may be used with the invention. In FIG. 3B, a source 110 of a carrier gas (helium in this example) is provided to a gas control system 370 of any type, which supply the gas at a controlled flow rate to CAP joint mixer 200. A conventional electrosurgical generator 350a supplies high frequency (HF) energy to a low frequency converter 350b, which outputs electrical energy having a frequency in the range of 10 kHz to 200 kHz and an output voltage in the range of 3 kV to 6 Kv.

Figure 3C:
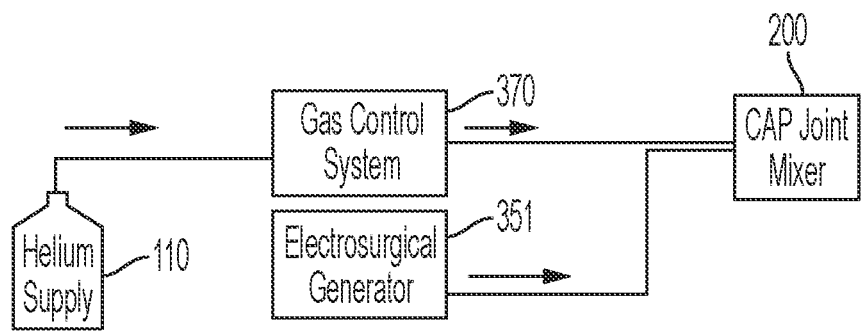
FIG. 3C is a block diagram of a plasma generator of another alternate preferred embodiment of the present invention.

Another embodiment, shown in FIG. 3C, has a carrier gas source 110 connected to a conventional gas control system 370, which in turn is connected to the CAP joint mixer 200, and a conventional electrosurgical generator 351 also connected to the CAP joint mixer 200.

Figure 4:
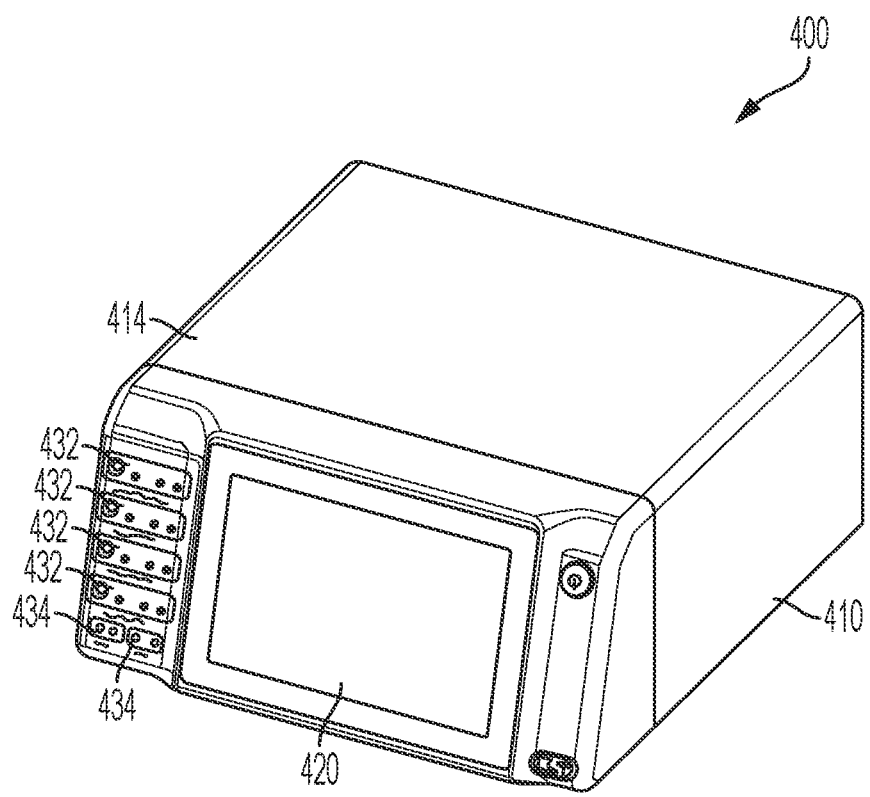
FIG. 4 is a perspective view of an integrated gas-enhanced electrosurgical generator of a preferred embodiment of the present invention.

A generator housing 400 for a CAP-enabled gas-enhanced electrosurgical generator 300 in accordance with a preferred embodiment of the present invention is shown in FIG. 4. The generator housing 400 has a housing 410 made of a sturdy material such as plastic or metal similar to materials used for housings of conventional electrosurgical generators. The housing 410 has a removable cover 414. The housing 410 and cover 414 have means, such as screws, tongue and groove, or other structure for removably securing the cover to the housing. The cover 414 may comprise just the top of the housing or multiple sides, such as the top, right side, and left side, of the housing 410. The housing 410 may have a plurality of feet or legs attached to the bottom of the housing. The bottom of the housing 410 may have a plurality of vents for venting from the interior of the gas-enhanced generator.

On the face of the housing 414 there is a touch-screen display 420 and a plurality of connectors 432, 434 for connecting various accessories to the generator, such as an argon plasma probe, a hybrid plasma probe, a cold atmospheric plasma probe, or any other electrosurgical attachment. The face of the housing 410 is at an angle other than 90 degrees with respect to the top and bottom of the housing 410 to provide for easier viewing and use of the touch screen display 420 by a user. One or more of the gas control modules may be mounted within a gas-enhanced electrosurgical generator 300.

The CAP-enabled gas-assisted electrosurgical generator has a graphical user interface (GUI) for controlling the components of the system using the touch screen display 420. The graphical user interface for example, may control robotics, argon-monopolar cut/coag, hybrid plasma cut, cold atmospheric plasma, bipolar, plasma sealer, hemo dynamics or voice activation. The graphical user interface further may be used with fluorescence-guided surgery. The graphical user interface (GUI) further may be used with guided imaging such as CT, MM, or ultrasound. The graphical user interface may communicate with RFID (such as may be found in various electrosurgical attachments) and may collect and store usage data in a storage medium. The graphical user interface communicates with the field-programmable gate array ("FPGA"), which may control an irrigation pump, insufflator, full bridge for adjusting the power output, fly back for regulating the power (DC to AC) and a foot pedal. The GUI further communicates with a database of data with associated predicted CAP settings or dosages via the CPU 310. The database storage may be internal memory or other internal storage 311 or external storage.

Figure 5:
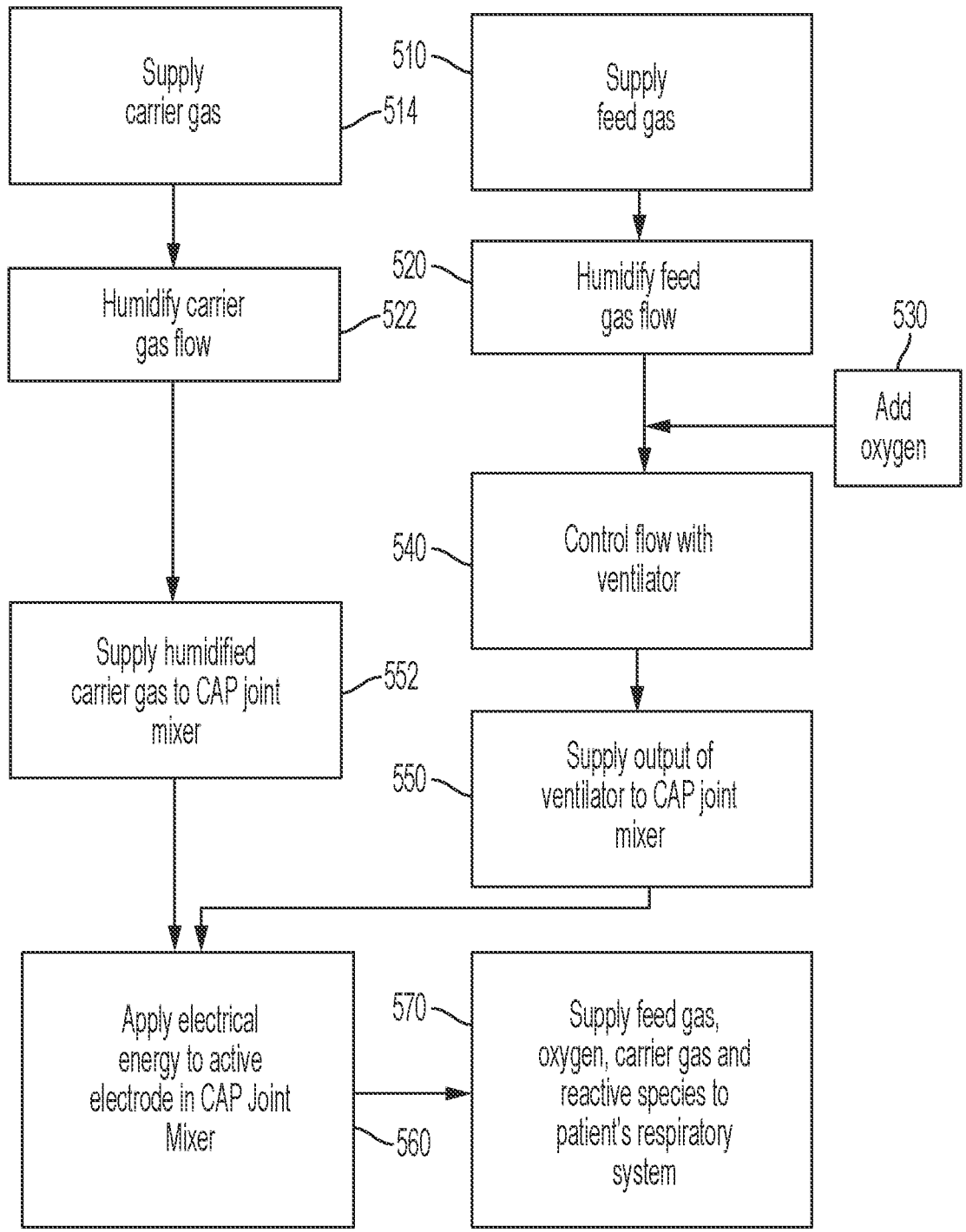
FIG. 5 is a flow diagram illustrating a method for treatment a respiratory infection according to a preferred embodiment of the present invention in which both a carrier gas and a feed gas are humidified.

A method for treatment of a respiratory infection according to a preferred embodiment of the present invention in which both the feed gas (air) and the carrier gas (helium) are humidified is described with reference to FIG. 5. Pressurized feed gas (air) is supplied to a humidifier 510. The pressurized air is humidified in a humidifier 520. Oxygen is added to the humidified air flow 530. The humidified air and oxygen flow is controlled by a ventilator or other respiratory delivery system 540. At the same time, a CAP carrier gas such as helium is supplied to a humidifier 514. The carrier gas is humidified in the humidifier 522. The humidified carrier gas is supplied to a CAP generator. The humidified CAP carrier gas from the CAP generator and the output of the ventilator both are supplied to a CAP joint mixer 550, 552. Electrical energy is applied to an inner electrode in the CAP joint mixer 560. The output of the CAP joint mixer is then supplied to the patient's respiratory system 570, for example, via a respiratory face mask, nasal cannula, or endobronchial tube.

In studies on the treatment of cancer using cold atmospheric plasma, it has been found that the CAP treatment decreases viability of cancer cells in a dose-dependent manner. Rowe, W., et al., "The Canady Helios Cold Plasma Scalpel Significantly Decreases Viability in Malignant Solid Tumor Cells in a Dose-Dependent Manner," Plasma, 2018. 1(1): p. 177-188.

Figure 6:
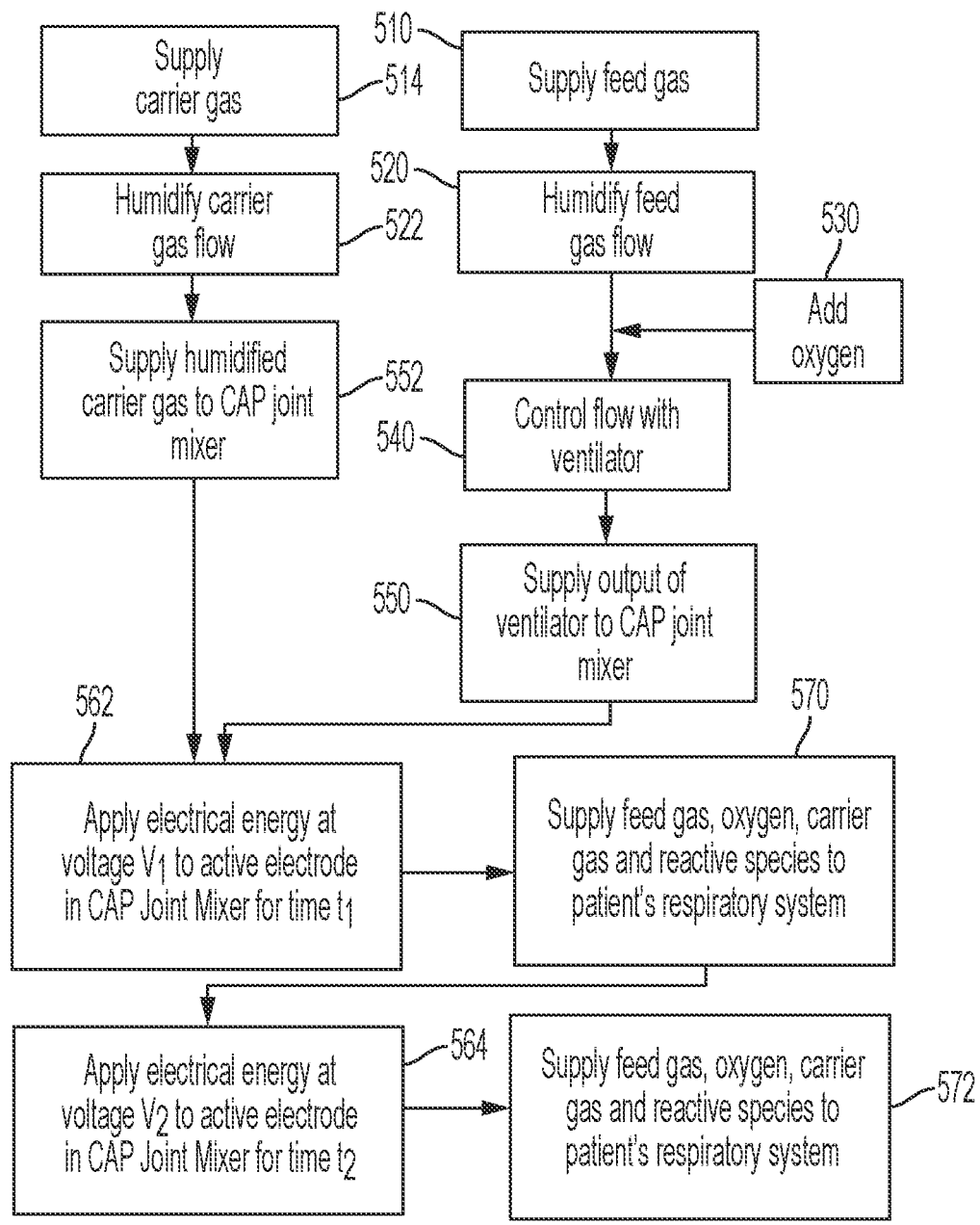
FIG. 6 is a flow diagram illustrating a method for treatment a respiratory infection according to a preferred embodiment of the present invention in which both a carrier gas and a feed gas are humidified and in which the CAP generator sweeps through a plurality of settings during a single treatment.

A method for treatment a respiratory infection according to another preferred embodiment of the present invention in which both the feed gas (air) and the carrier gas (helium) are humidified is described with reference to FIG. 6. In this embodiment, rather than electrical energy being applied to the inner electrode in the CAP joint mixer at a single setting (e.g., 70 V) for the entire treatment time (step 560 in FIG. 5), the generator automatically sweeps thought a plurality of settings applying a first setting (e.g., 70 V) for a first time $t_1$ 562 while supplying the output to the patient 570 and then applying a second setting (e.g., 40 V) for a second time $t_2$ 564 while supplying the output to the patient 572.

An alternative embodiment of a system 700 is referred to herein as the "Helium Gas Humidity Adjustment Setup" is described with reference to FIG. 7A. A helium gas source 110 is split into two lines 112, 114, with each of the two lines controlled by a mass flow controller (MFC) 120. The Helium gas flow (50 to 1000 mL/min) in line 112 is passed through an $H_2O$ filled container (Humidifier 130) and then is fed into a mixing chamber 140. The helium gas flow in the line 114 is fed directly into the mixing chamber 140. In this manner, with the mass flow controllers 120 on the lines 112, 114 a relative $H_2O$ saturation in the gas exiting the chamber 140 can be adjusted. Adjustment of the gas flow in the two lines 112, 114 makes the overall flow rate and humidity fine tuning of the gas flow exiting the chamber 140 possible. The humidity may be in the range of 20%-100% with a preferred humidity of at least 70%. The total helium flow in this embodiment could be varied from 0.5 L/min to 5 L/min in all cases. In this Helium Gas Humidity Adjustment Setup, the Helium $H_2O$ vapor content was varied during experiments. The humidity of Helium gas in the chamber 140 was measured via calibrated High-Accuracy Humidity and Temperature Meter 142 as shown in the FIG. 7A. The humidified helium gas from the chamber 140 is fed into a CAP generator 300, At the same time, an un-humidified air tank 150 and un-humidified oxygen tank 160 feed air and oxygen respectively to a respiratory delivery system 170, such as a ventilator, CPAP (continuous positive airway pressure) system, or BIPAP (Bilevel Positive Airway Pressure) system. These are referred to herein as "feed gases." The respiratory delivery system 170 will mix, adjust, and measure the pressure, flow rate, ratio, and frequency of the patient inbreath of air, oxygen, and $CO_2$. The output of the CAP generator 300 and the respiratory delivery system 170 are connected to a dielectric barrier discharge (DBD) assembly 200. The output of the CAP joint mixer 200 is connected to a delivery member 190, which, for example, may be an endobronchial tube, oxygen CPAP (continuous positive airway pressure), BIPAP (Bilevel Positive Airway Pressure), ventilator face mask, or nasal $O_2$ cannula 190 to deliver reactive species 192, e.g., H2O2, NO2—, NO3—, ONOO—, and O2-, generated by the system into the patient's respiratory system.

Figure 7A:
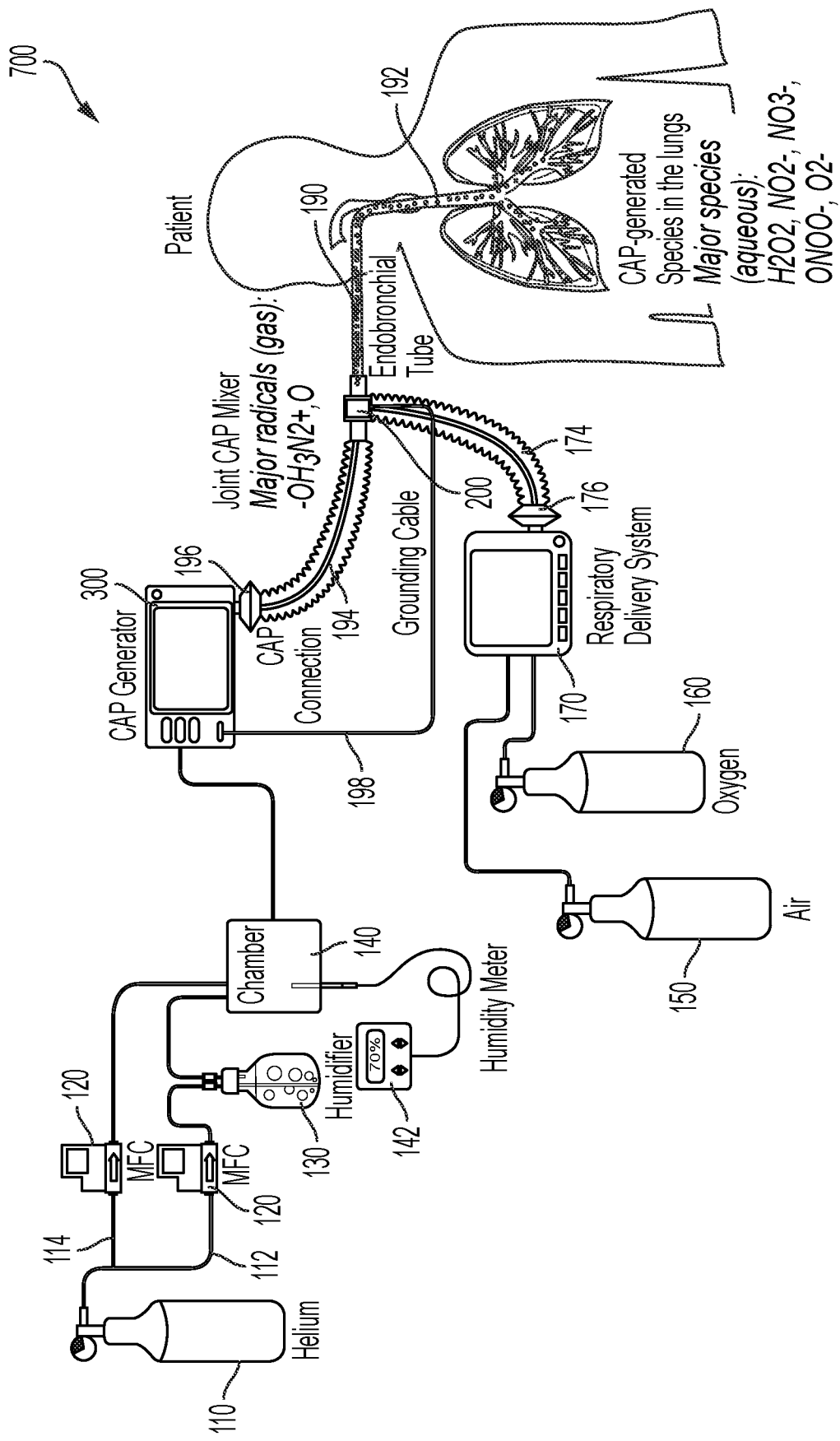
FIG. 7A is a block diagram of a cold atmospheric plasma system having a CAP Joint Mixer for treatment of respiratory infections in accordance with a second preferred embodiment in which a carrier gas is humidified.
Figure 7B:
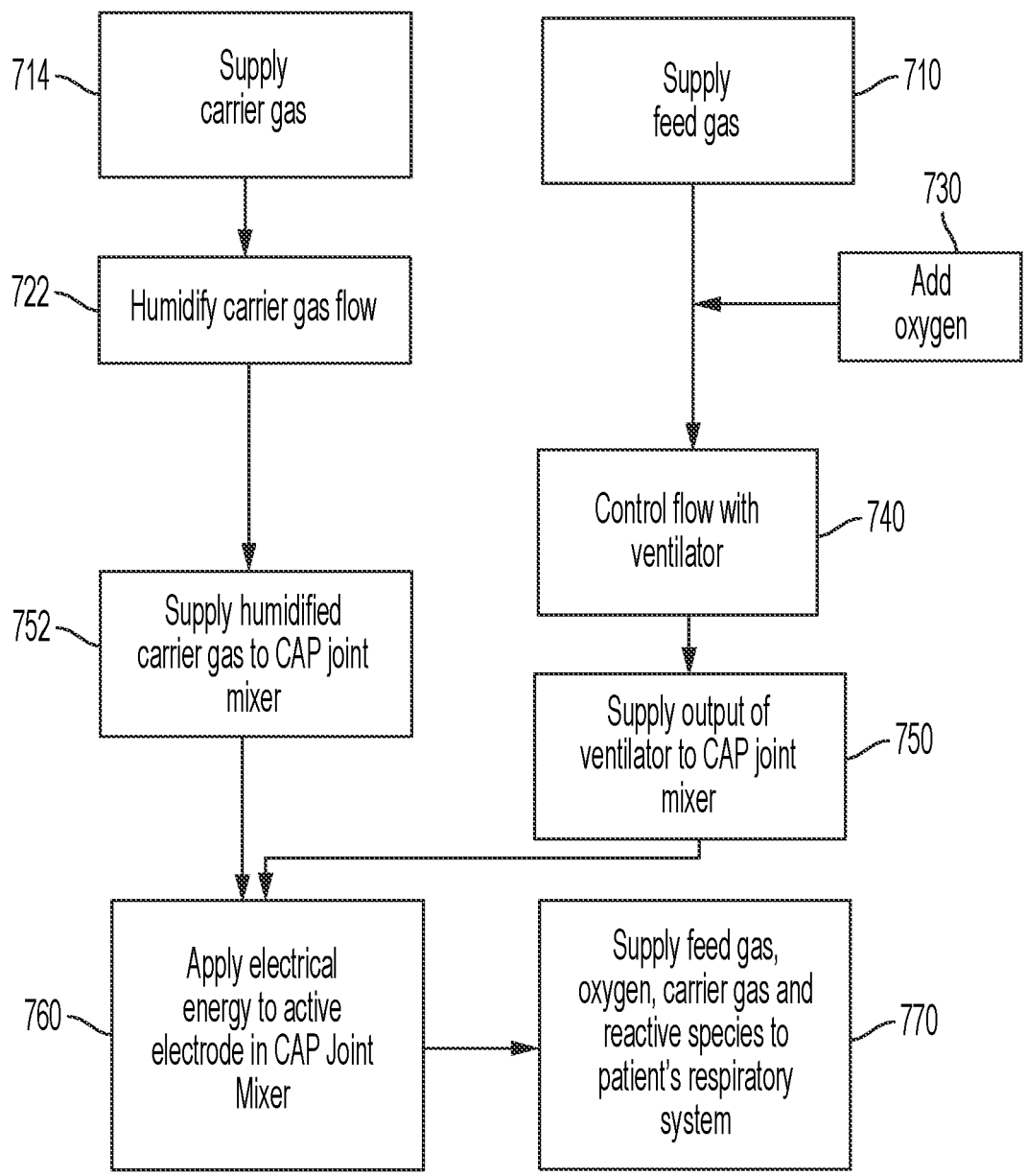
FIG. 7B is a flow diagram illustrating a method for treatment of a respiratory infection according to a preferred embodiment of the present invention in accordance with a second preferred embodiment in which a carrier gas is humidified.

A method for treating a respiratory infection with the system of FIG. 7A is described with reference to FIG. 7B. A CAP carrier gas such as helium is supplied to a humidifier 714. The carrier gas is humidified 722. The humidified carrier gas is supplied to a CAP generator. At the same time, pressurized feed gas (air) is supplied 710. Oxygen is added to the air flow 730. The air and oxygen flow is controlled by a ventilator or other respiratory delivery system 740. The humidified CAP carrier gas from the CAP generator and the output of the ventilator both are supplied to a CAP joint mixer 750, 752. Electrical energy is applied to an inner electrode in the CAP joint mixer 760. The output of the CAP joint mixer is then supplied to the patient's respiratory system 770, for example, via a respiratory face mask, nasal cannula, or endobronchial tube.

Figure 8A:
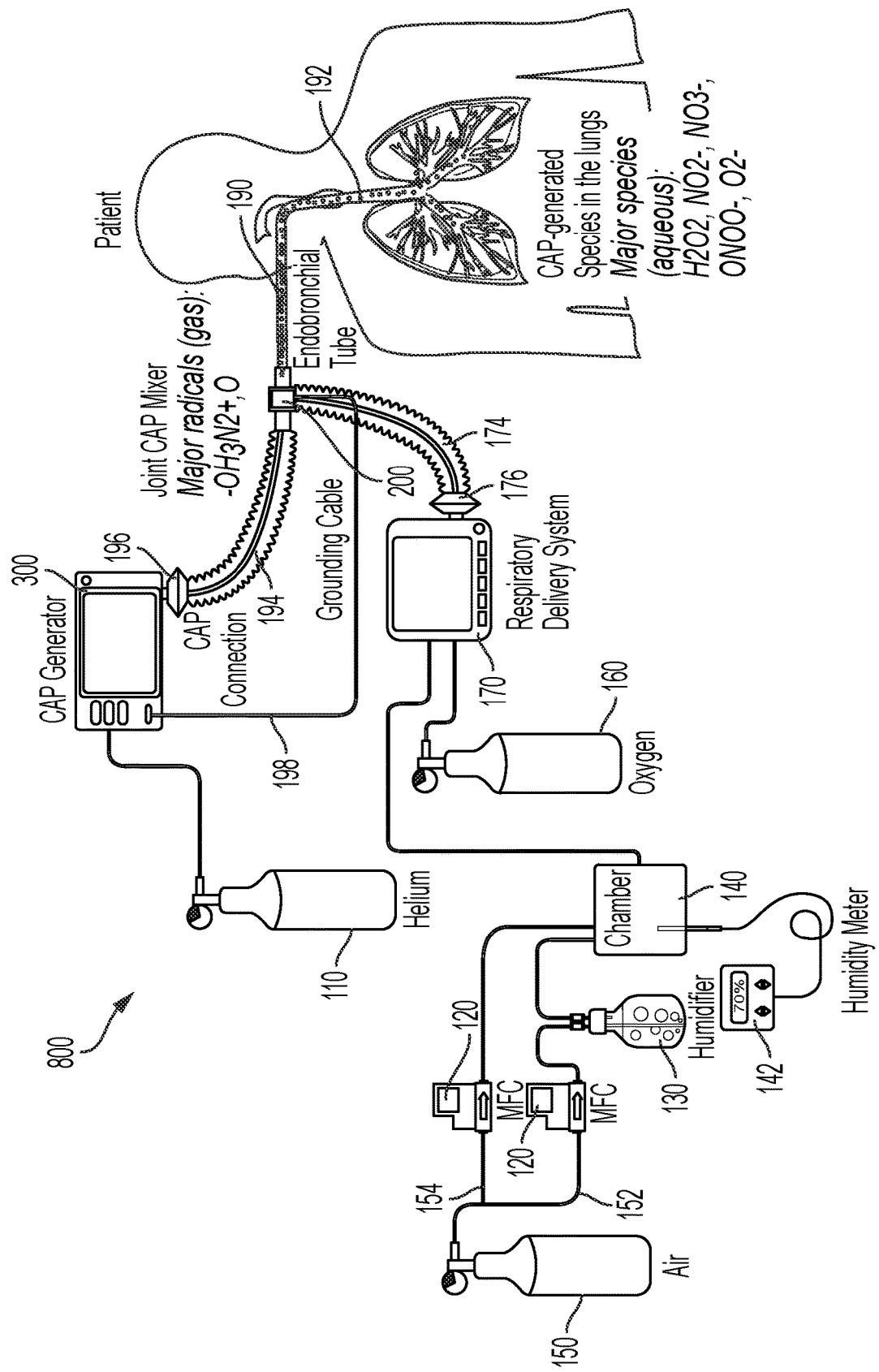
FIG. 8A is a block diagram of a cold atmospheric plasma system having a CAP Joint Mixer for treatment of respiratory infections in accordance with a third preferred embodiment in which a feed gas is humidified.

Another embodiment of a cold atmospheric plasma system 800 for treatment of respiratory infections is described with reference to FIG. 8A. A helium gas source 110 is fed into an electrosurgical generator 300. At the same time, an un-humidified air supply 150 (feed gas) is split into two lines 152, 154. Each line 152, 154 is controlled by a mass flow controllers (MFC) 120. The air gas flow in line 152 is passed through an $H_2O$ filled container (Humidifier 130) and then is fed into a mixing chamber 140. The air gas flow in the line 114 is fed directly into the mixing chamber 140. In this manner, with the mass flow controllers 120 on the lines 152, 154 a relative $H_2O$ saturation in the air feed exiting the chamber 140 can be adjusted. Adjustment of the air flow in the two lines 152, 154 makes the overall flow rate and humidity fine tuning possible. The humidity may be in the range of 20%-100% with a preferred humidity of at least 70%. The humidity of air in the chamber 140 is measured via calibrated High-Accuracy Humidity and Temperature Meter 142. The humidified air from the chamber 140 and oxygen from an oxygen supply 160 are provided to a respiratory delivery system 170, such as a ventilator, CPAP machine, BIPAP machine, or other known respiratory deliver system. The respiratory delivery system 170 will mix, adjust and measure the pressure, flowrate, ratio and frequency of the patient inbreath of exhaust air, oxygen and CO2.

The output of the CAP joint mixer 200 is connected to a delivery member 190, which, for example, may be an endobronchial tube, oxygen CPAP (continuous positive airway pressure), BIPAP (Bilevel Positive Airway Pressure), ventilator face mask, or nasal $O_2$ cannula 190 to deliver reactive species 192, e.g., H2O2, NO2—, NO3—, ONOO—, and O2-, generated by the system into the patient's respiratory system.

Figure 8B:
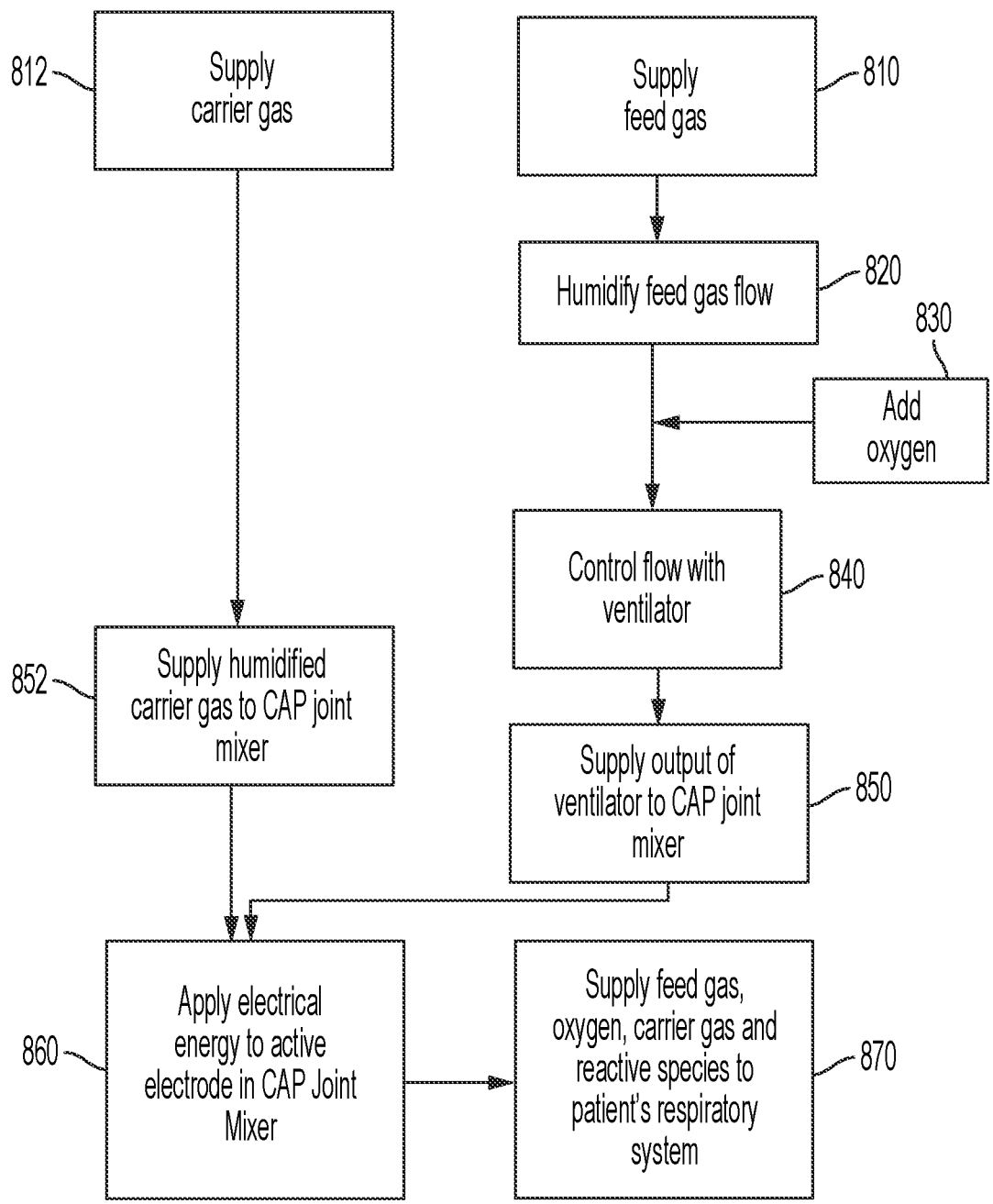
FIG. 8B is a flow diagram illustrating a method for treatment of a respiratory infection according to a preferred embodiment of the present invention in accordance with a third preferred embodiment in which a feed gas is humidified.

A method for treatment a respiratory infection according to a preferred embodiment of the present invention in which the feed gas (air) is humidified is described with reference to FIG. 8B. Pressurized feed gas (air) is supplied to a humidifier 810. The pressurized air is humidified in a humidifier 820. Oxygen is added to the humidified air flow 830. The humidified air and oxygen flow is controlled by a ventilator or other respiratory delivery system 840. At the same time, a CAP carrier gas such as helium is supplied to a CAP generator 812. The CAP carrier gas from the CAP generator and the output of the ventilator both are supplied to a CAP joint mixer 850, 852. Electrical energy is applied to an inner electrode in the CAP joint mixer 860. The output of the CAP joint mixer is then supplied to the patient's respiratory system 870, for example, via a respiratory face mask, nasal cannula, or endobronchial tube. Other embodiments of the invention are possible in which the plasma is delivered to a patient, for example, through an endoscopic or laparoscopic device. Still further, in other embodiments, the present invention may treat cancer in the abdomen by feeding the output of the CAP joint mixer into the abdomen, for example, via a laparoscope or trocar.

Figure 9:
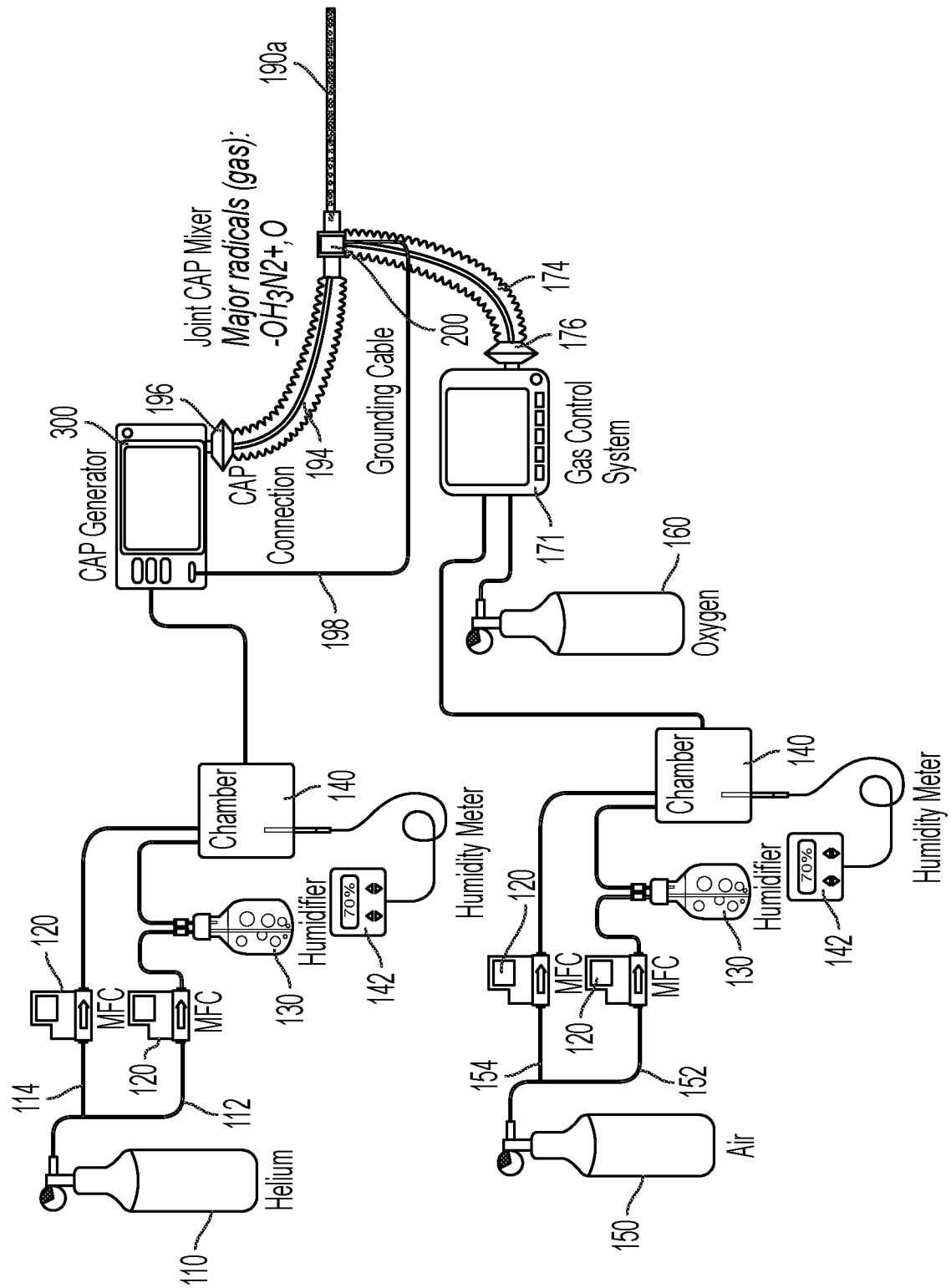
FIG. 9 is a block diagram of a cold atmospheric plasma system having a CAP Joint Mixer for endoscopic or laparoscopic uses in accordance with a preferred embodiment.

A cold atmospheric plasma system for treatment of a patient via an endoscope or laparoscope in accordance with a preferred embodiment of the present invention is described with reference to FIG. 9. A helium gas source 110 is split into two lines 112, 114, with each of the two lines controlled by a mass flow controller (MFC) 120. The Helium gas flow (50 to 1000 mL/min) in line 112 is passed through an $H_2O$ filled container (Humidifier 130) and then fed into a mixing chamber 140. The helium gas flow in the line 114 is fed directly into the mixing chamber 140. In this manner, with the mass flow controllers 120 on the lines 112, 114 a relative $H_2O$ saturation in the gas exiting the chamber 140 can be adjusted. Adjustment of the gas flow in the two lines 112, 114 makes the overall flow rate and humidity fine tuning of the gas flow exiting the chamber 140 possible. The humidity may be in the range of 20%-100% with a preferred humidity of at least 70%. The total helium flow in this embodiment could be varied from 0.5 L/min to 5 L/min in all cases. The humidity of Helium gas in the chamber 140 is measured via calibrated High-Accuracy Humidity and Temperature Meter 142. The humidified helium gas from the chamber 140 is fed into an electrosurgical generator 300. A variety of electrosurgical generators are known in the art and could be used with the present invention. The gas being fed into the Cold Atmospheric Plasma (CAP) Generator 300 is referred to herein as the "carrier gas."

Figure 3D:
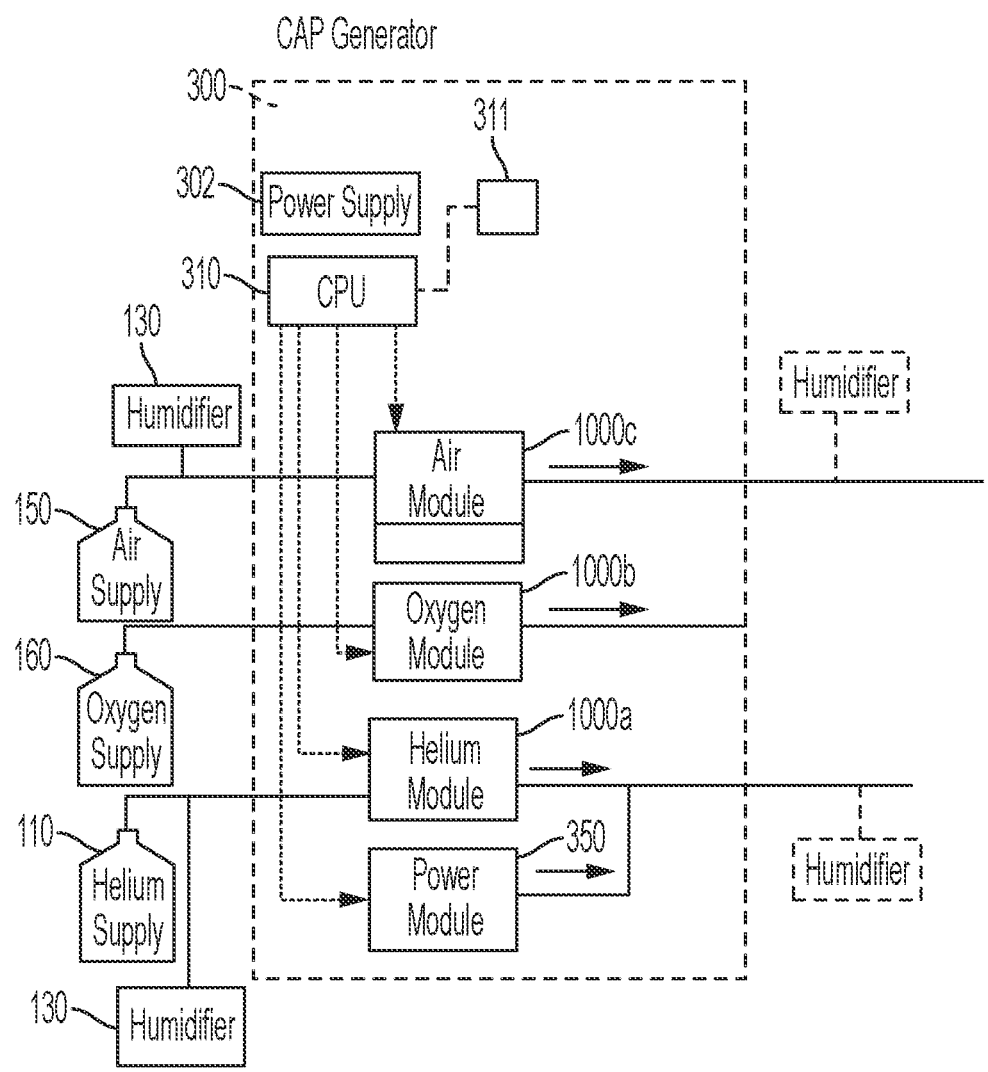
FIG. 3D is a block diagram of an integrated gas-enhanced electrosurgical generator having a plurality of gas modules of another alternate preferred embodiment of the present invention.

At the same time, an un-humidified air supply 150 (feed gas) is split into two lines 152, 154. Each line 152, 154 is controlled by a mass flow controllers (MFC) 120. The air gas flow in line 152 is passed through an $H_2O$ filled container (Humidifier 130) and then is fed into a mixing chamber 140. The air gas flow in the line 154 is fed directly into the mixing chamber 140. In this manner, with the mass flow controllers 120 on the lines 152, 154 a relative $H_2O$ saturation in the air feed exiting the chamber 140 can be adjusted. Adjustment of the air flow in the two lines 152, 154 makes the overall flow rate and humidity fine tuning possible. The humidity may be in the range of 20%-100% with a preferred humidity of at least 70%. The humidity of air in the chamber 140 is measured via calibrated High-Accuracy Humidity and Temperature Meter 142. Humidified air from the chamber 140 and oxygen from an oxygen supply 160 are connected to a gas control system 171. In an alternative embodiment, an integrated gas-enhanced electrosurgical generator having a plurality of gas control modules 1000a, 1000b, 1000c such as is shown in FIG. 3D may be used. In such a system the flow helium, air and oxygen all are controlled by gas modules in a single housing and having a unified control system.

The output of the CAP generator 300 and humidified air and oxygen from the gas control system 170 are connected to a dielectric barrier discharge (DBD) assembly 200, referred to herein as a "CAP joint mixer." A ground cable 198 connects an outer electrode of the CAP joint mixer 200 to a ground in the CAP generator 200. While the grounding cable 198 is shown separate from the tubing 194 in FIG. 1, other arrangements are possible in which the ground cable 198 is combined, for example, in a harness with the tubing 194. Due to the presence of the $H_2O$, the ionization of Helium and $H_2O$ to $He^+ + e^- + e^-$ chemical reaction will happen simultaneously. The cold plasma-generated reactive species ($H2O2$, $NO2-$, $NO3-$, $ONOO-$, and $O2-$) are produced.

The output of the CAP joint mixer 200 is connected to an elongated delivery member 190a, which, for example, may be a rigid or flexible tube of a size that will fit into a channel of any type of endoscope or laparoscope, whether the scope is a bronchoscope, colonoscope or any other type of scope used in surgical applications.

Figure 2A:
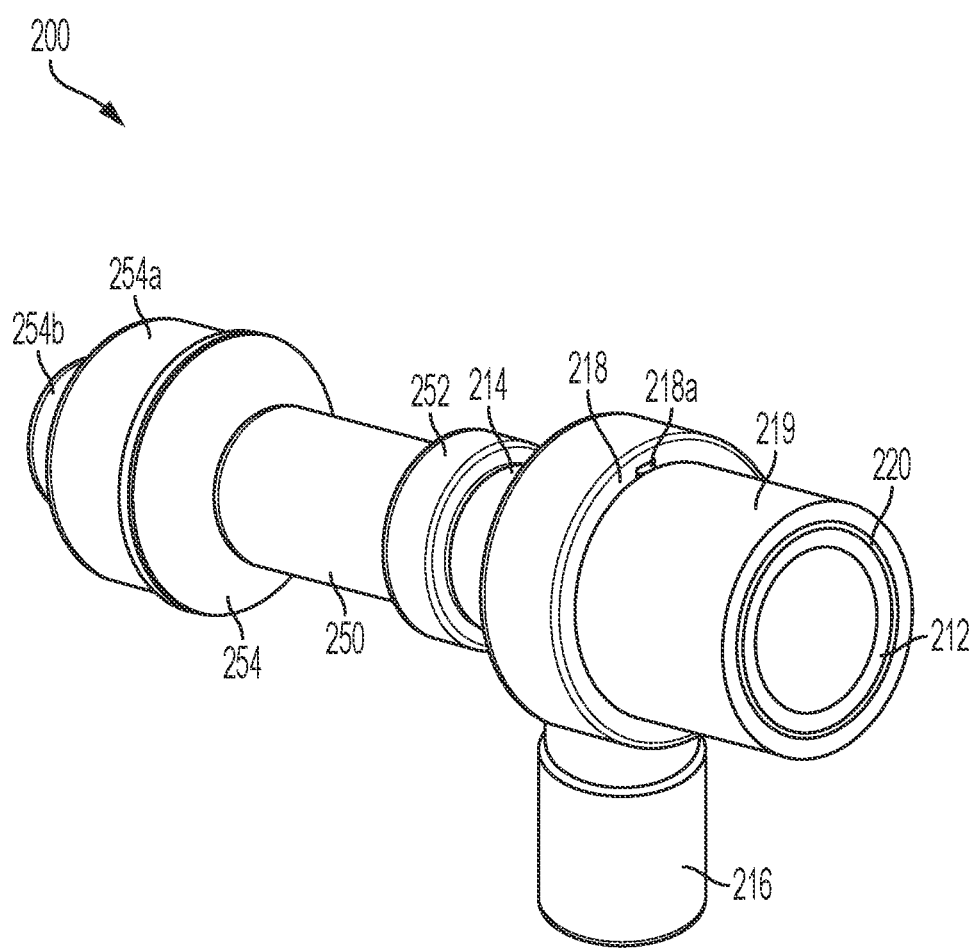
FIG. 2A is an isometric view of a preferred embodiment of a CAP joint mixer or dielectric barrier discharge (DBD) assembly in accordance with the preferred embodiments of the present invention.
Figure 2B:
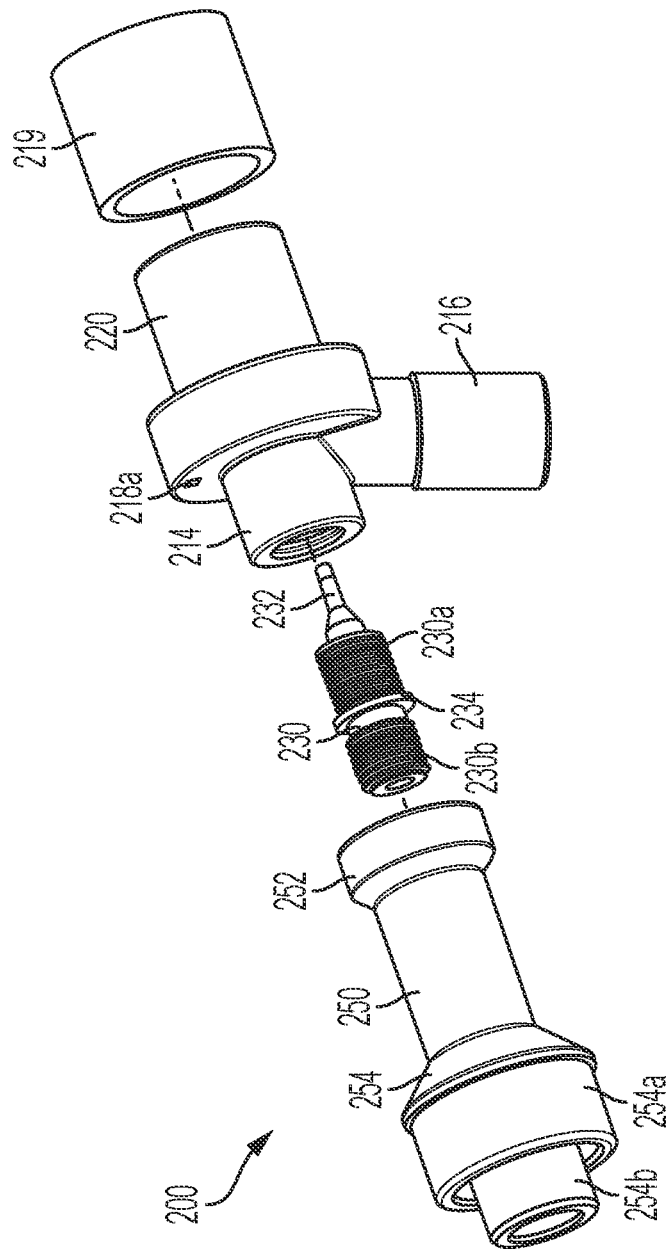
FIG. 2B is An exploded view of a preferred embodiment of a CAP joint mixer or dielectric barrier discharge (DBD) assembly in accordance with the preferred embodiments of the present invention.
Figure 2C:
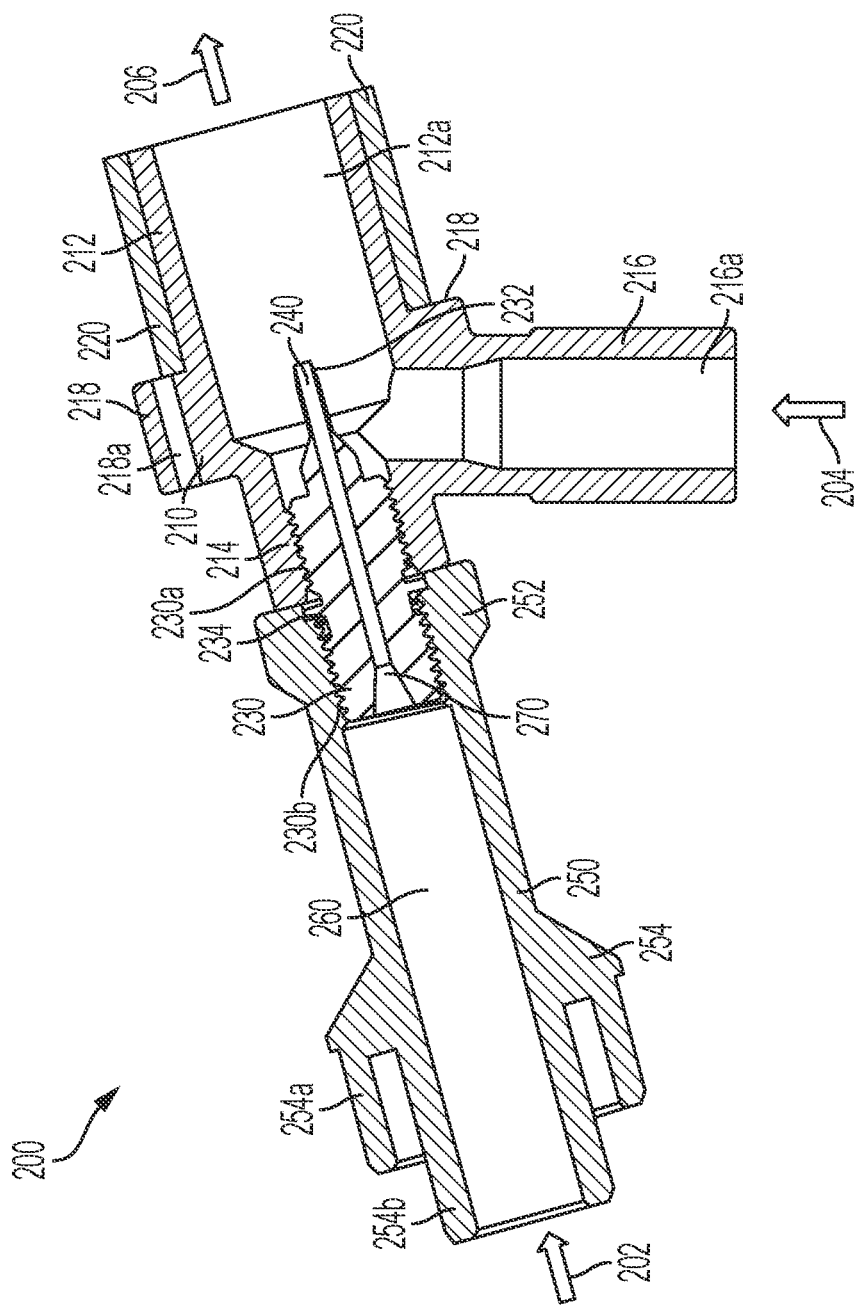
FIG. 2C is a partial cross-sectional view of a preferred embodiment of a CAP joint mixer or dielectric barrier discharge (DBD) assembly in accordance with the preferred embodiments of the present invention.
Figure 2D:
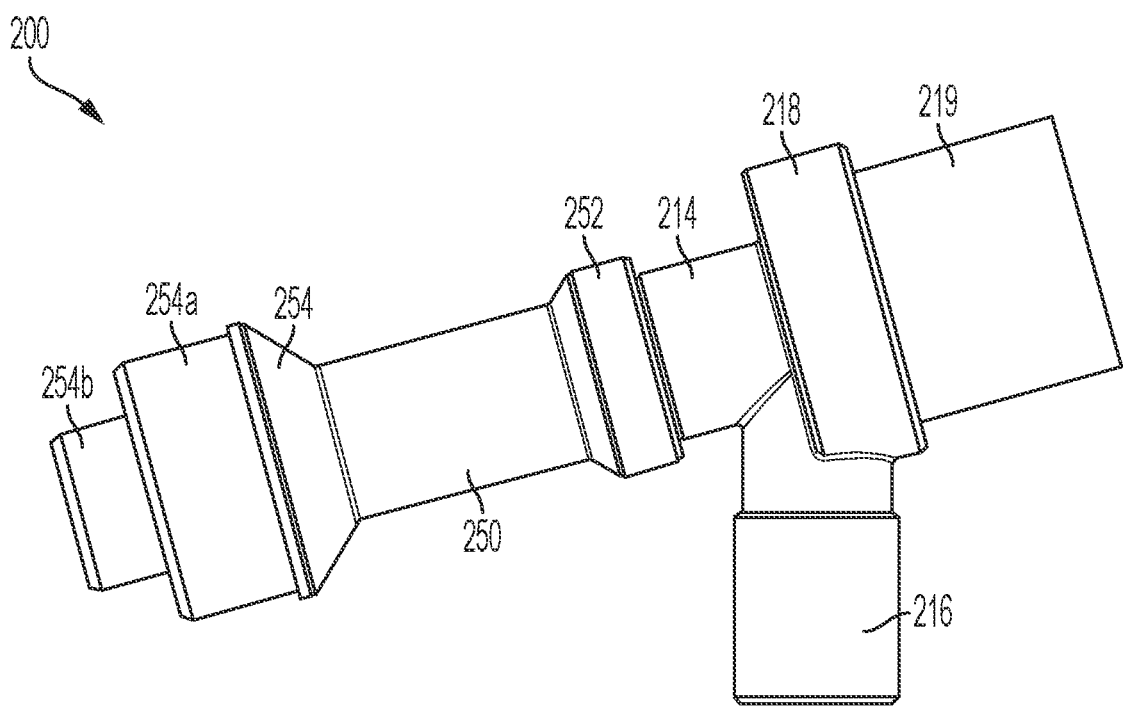
FIG. 2D is a front view of a preferred embodiment of a CAP joint mixer or dielectric barrier discharge (DBD) assembly in accordance with the preferred embodiments of the present invention.
Figure 2E:
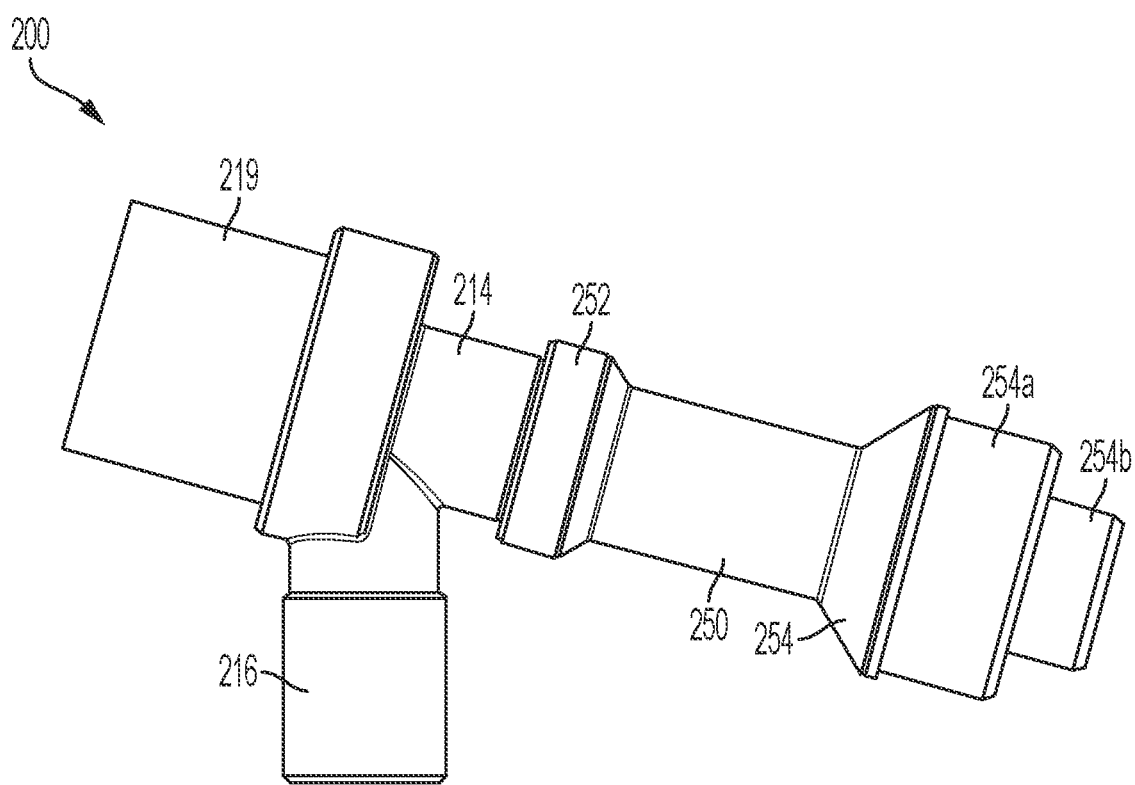
FIG. 2E is a back view of a preferred embodiment of a CAP joint mixer or dielectric barrier discharge (DBD) assembly in accordance with the preferred embodiments of the present invention.
Figure 2F:
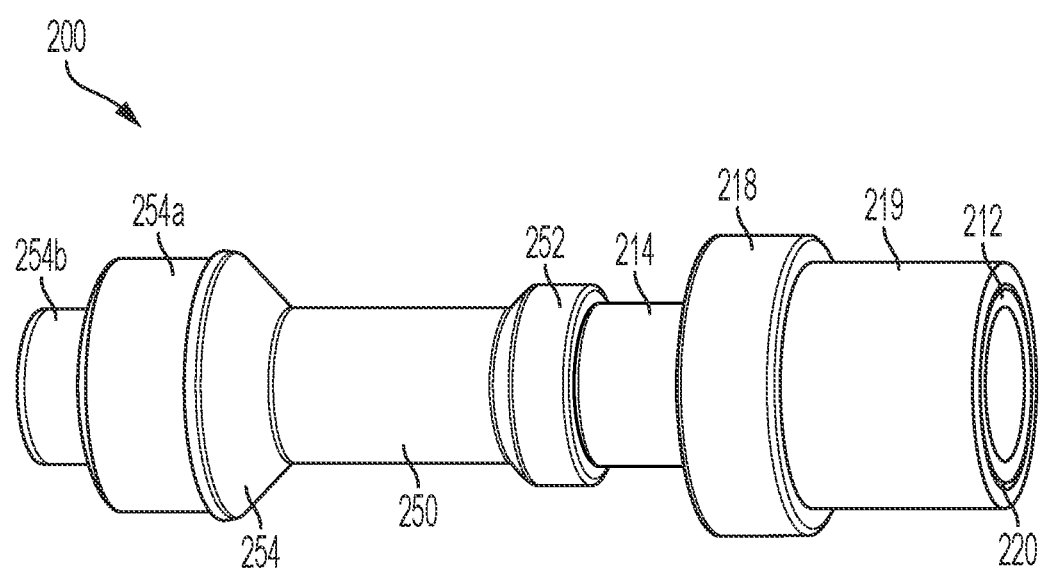
FIG. 2F is a top view of a preferred embodiment of a CAP joint mixer or dielectric barrier discharge (DBD) assembly in accordance with the preferred embodiments of the present invention.
Figure 2G:
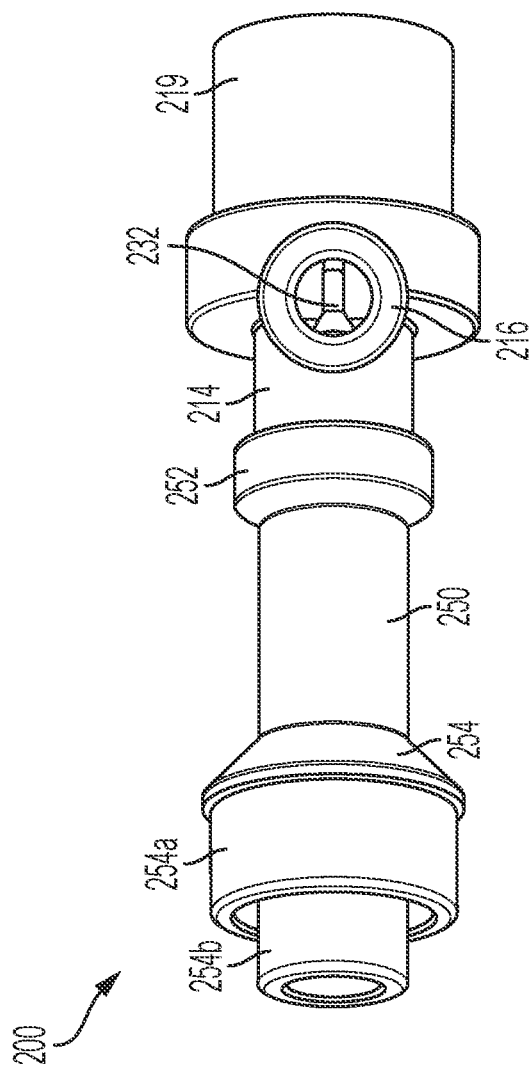
FIG. 2G is a bottom view of a preferred embodiment of a CAP joint mixer or dielectric barrier discharge (DBD) assembly in accordance with the preferred embodiments of the present invention.
Figure 2H:
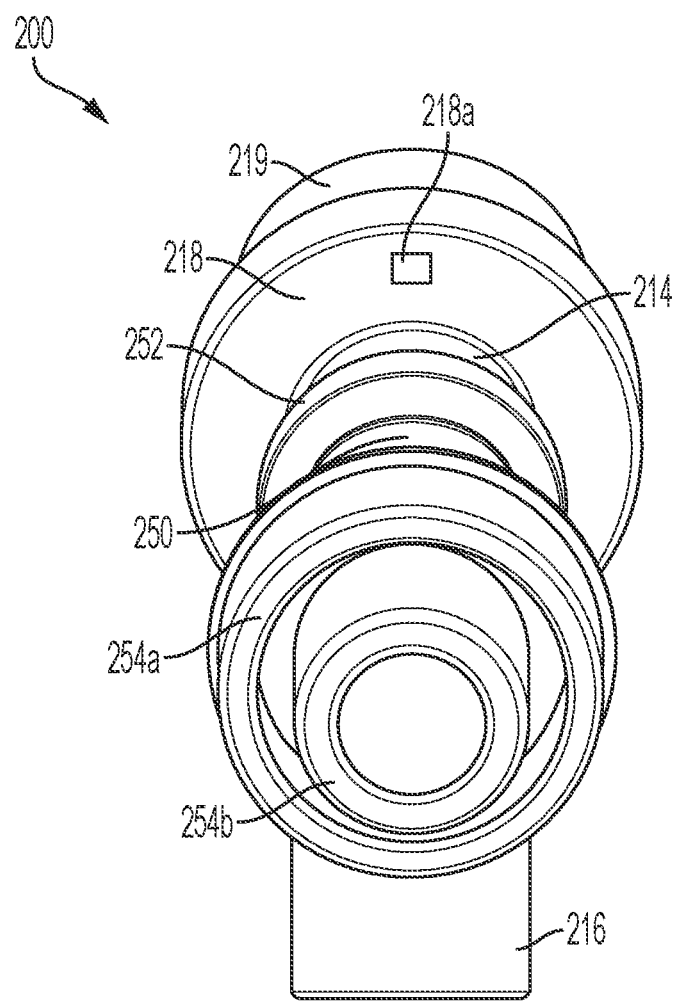
FIG. 2H is a left side view of a preferred embodiment of a CAP joint mixer or dielectric barrier discharge (DBD) assembly in accordance with the preferred embodiments of the present invention.
Figure 21:
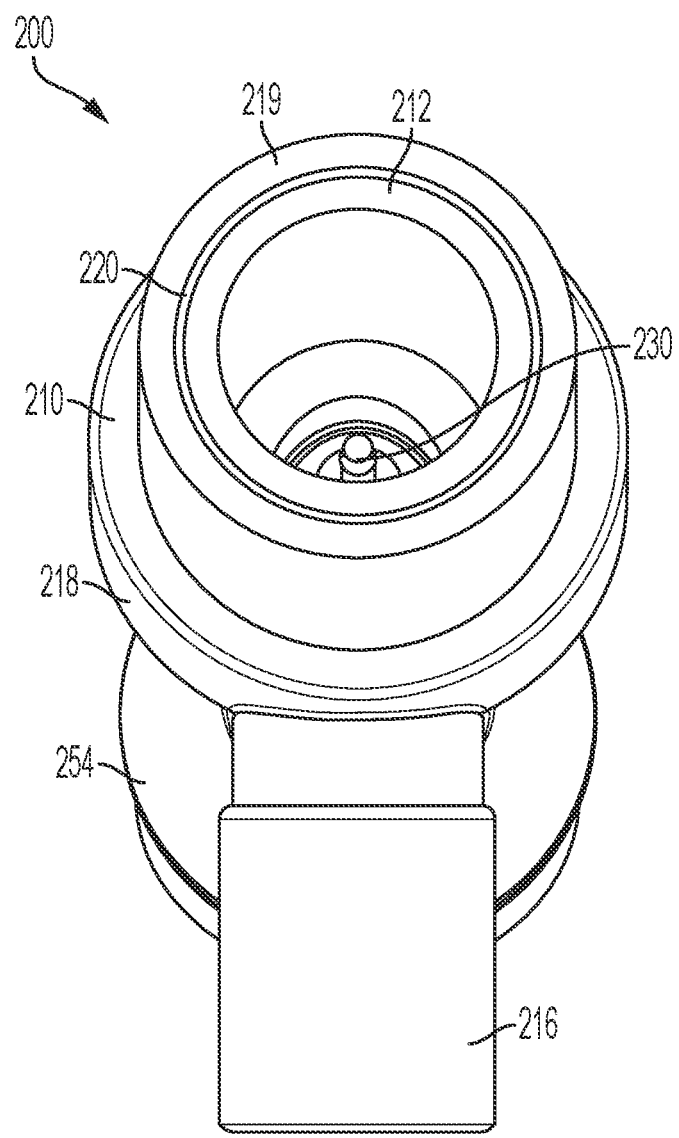

The embodiment shown in FIG. 1A where both the feed gas (air) and the carrier gas (helium) are humidified provides greater humidity in CAP joint mixer than embodiments where only one of the feed gas and carrier gas is humidified. In the embodiment of FIG. 1A, experiments have shown that due to the increased humidity, the treatment time necessary to achieve a 100% kill rate for lung cancer cells can be reduced to 5 minutes versus about 17 minutes for the embodiments where only one of the feed gas and carrier gas is humidified. Further, the production of ozone can be reduced from roughly 20 ppm (parts per million) for the embodiments of FIGS. 7A and 8A to less than 3 ppm (approximately 2 ppm) in the embodiment of FIG. 1A.

A gas control module 1000 in accordance with the present invention is designed for gas-enhanced electrosurgical systems. Conventionally, gas-enhanced electrosurgical systems have an electrosurgical generator and a gas control unit that have separate housings. The conventional gas control unit typically controls only a single gas such as argon, $CO_2$ or helium. The present invention uses a gas control module 1000 that may be used in a gas control unit or in a combined unit functioning both as an electrosurgical generator and as a gas control unit. Further, a plurality of gas control modules in accordance with the present invention may be combined in a single gas control unit or combination generator/gas control unit to provide control of multiple gases and provide control for multiple types of gas-enhanced surgery such as argon gas coagulation, hybrid plasma electrosurgical systems and cold atmospheric plasma systems.

Still further, while helium is the carrier gas used in the disclosed embodiments, other gases such as argon, nitrogen, oxygen or air may be used as a carrier gas.

While the preferred embodiments are described with a ventilator, other medical respiration devices such as a continuous positive airway pressure (CPAP) system could be used with the present invention.

Experiments

The cold atmospheric plasma system for treatment of respiratory infections where only the air was humidified was used to treat 1 mL phosphate buffer saline (PBS) in 12-well plates with the generator in Argon Coag Mode and Spray Mode operating at a frequency near 100 kHz for 3 min each. Voltage was set to be 70 V. Oxygen and air flow rate were both set to be 1 LPM. The mixture of oxygen ($O_2$) and air was humidified by bubbling through DI water. The relative humidity (RH) of the mixture is about 80%. Flow rate of helium, the carrier gas for cold atmospheric plasma (CAP), was set at 3 LPM. Therefore, the $O_2$ percentage of the final output gas from the endobronchial tube was about 24% in the $O_2$-air-He mixture.

Among of the cocktail of plasma-generated reactive oxygen species (ROS) and reactive nitrogen species (RNS) in the treated solution, hydrogen peroxide ($H_2O_2$) and nitrite ($NO_2^-$) are the most commonly studied long-lived species. Their concentrations were measured in treated phosphate-buffered saline (PBS) using Griess Reagent System (Promega, G2930) and colorimetric Hydrogen Peroxide Assay Kit (Sigma-Aldrich, MAK311-1KT) with CAP on or off. Results were read by a BioTek microplate reader at 550 nm and 595 nm for absorbance, respectively.

Electrosurgical generators typically have multiple modes of operation, including "cut" or cutting modes and "coag" or coagulation modes of operation. A cut mode typically will have a low voltage waveform form (e.g., 1 KV) with a high duty cycle, e.g. 100%. The coag mode of an electrosurgical generator typically creates a waveform with large amplitude but short duration "spikes" to achieve hemostasis (coagulation). For example, a coag mode on an electrosurgical generator may use a high voltage wave form at a 6% duty cycle. Different degrees of hemostasis (coagulation) can be achieved by utilizing varying degrees of "Blended" waveforms, e.g., 50% on/50% off, 40% on/60% off, or 25% on/75% off. Electrosurgical generators also have argon plasma coagulation modes, or "argon coag" modes. Argon Plasma Coagulation (APC) utilizes plasma produced by the ionization of a few millimeter diameter argon flow exhausting into ambient air from the electrosurgical hand-piece. When compared to a cut mode, an argon coagulation mode on a generator may use a high voltage (e.g., 4 KV for argon coag versus 1 KV for a cut mode), less current (e.g., 200 mA for argon coag versus 500 mA for cut), and lower frequency (30 KHz for argon coag versus 390 KHz for cut). Electrosurgical generators also have a "Spray Mode," which is similar to the argon coag mode (similar voltage and current), but they have a random week of frequency, for example, from 10-30 KHz, which allows it to cover different tissue impedances.

Figure 10A:
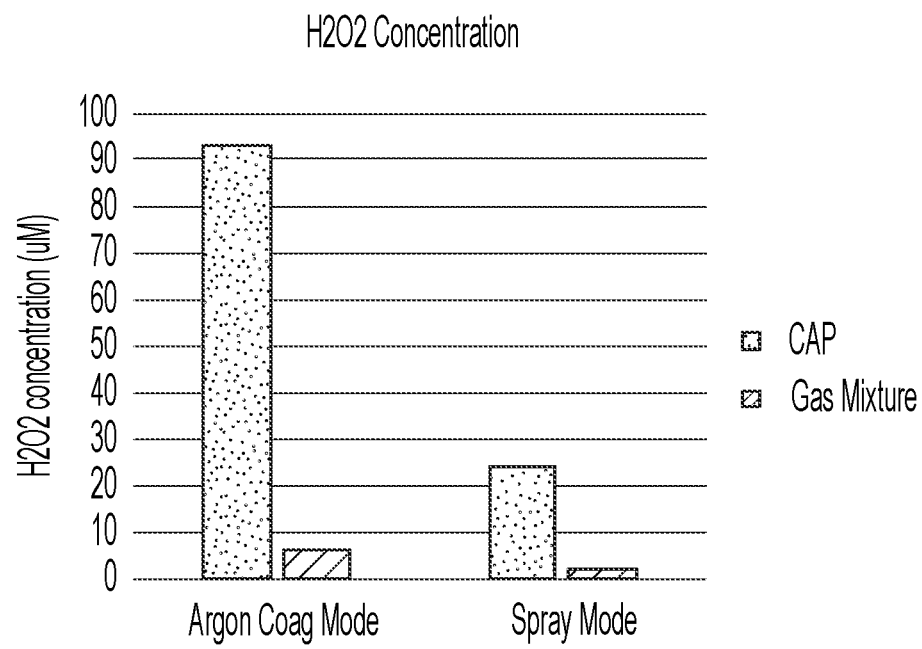
FIGS. 10A and 10B are graphs of the concentrations of $H_2O_2$ and $NO_2^-$ with the cold atmospheric plasma system for treatment of respiratory infections of FIG. 1C.
Figure 10B:
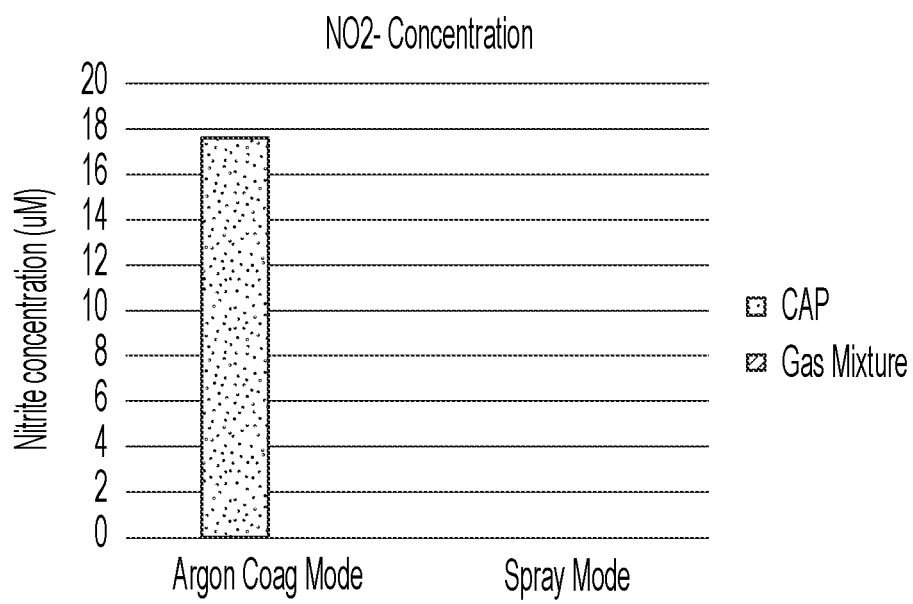
Figure 10C:
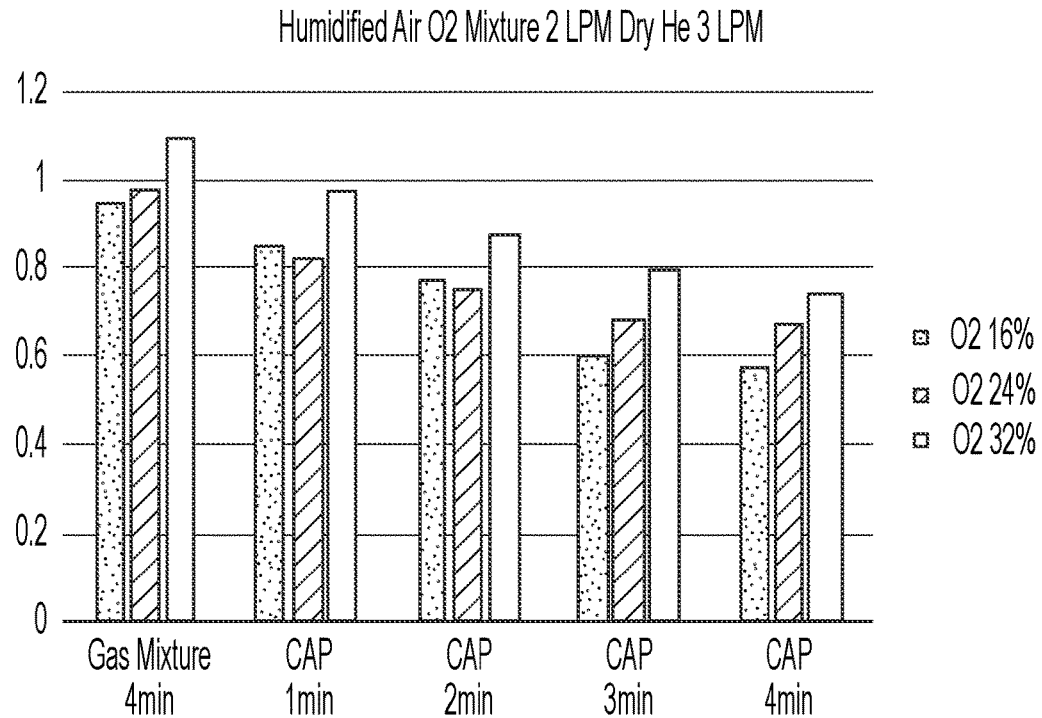
FIG. 10C is a graph of viability of A549 cells treated by the present invention with humidified $O_2$ and air mixture and various $O_2$ percentage for up to 4 minutes.
Figure 10D:
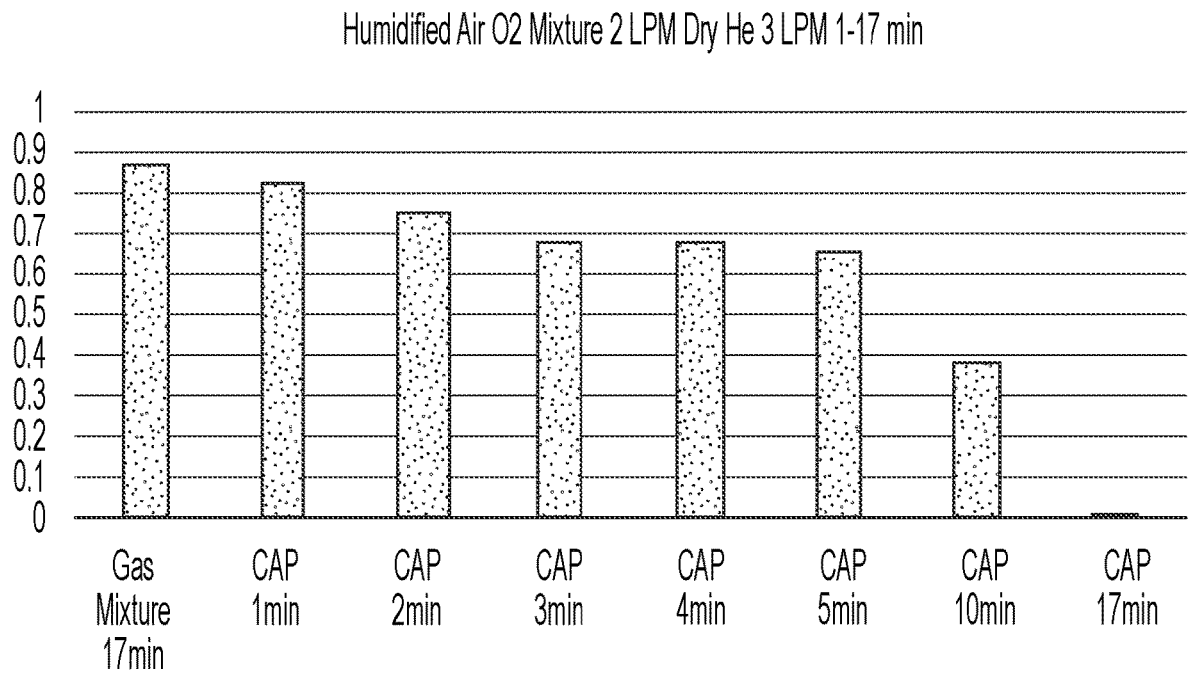
FIG. 10D is a graph of viability of A549 cells treated by the present invention with humidified Air/$O_2$ mixture and dry He with 24% $O_2$ for up to 17 minutes.
Figure 10E:
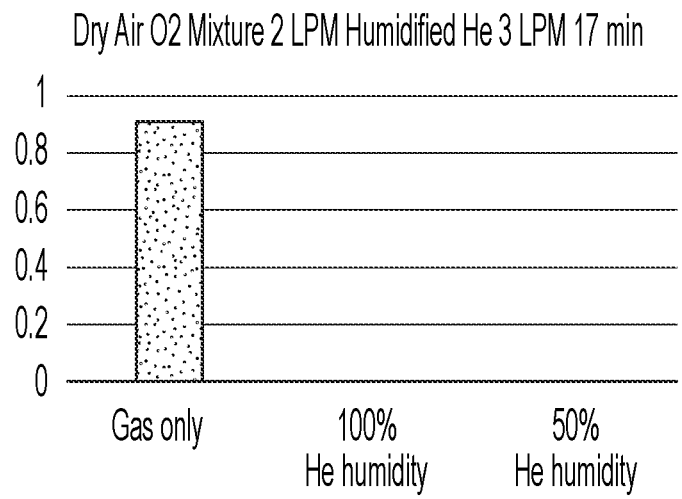
FIG. 10E is a graph of viability of A549 cells treated by the present invention with humidified helium and dry $O_2$ and air mixture (with 24% $O_2$) for 17 minutes.
Figure 14A:
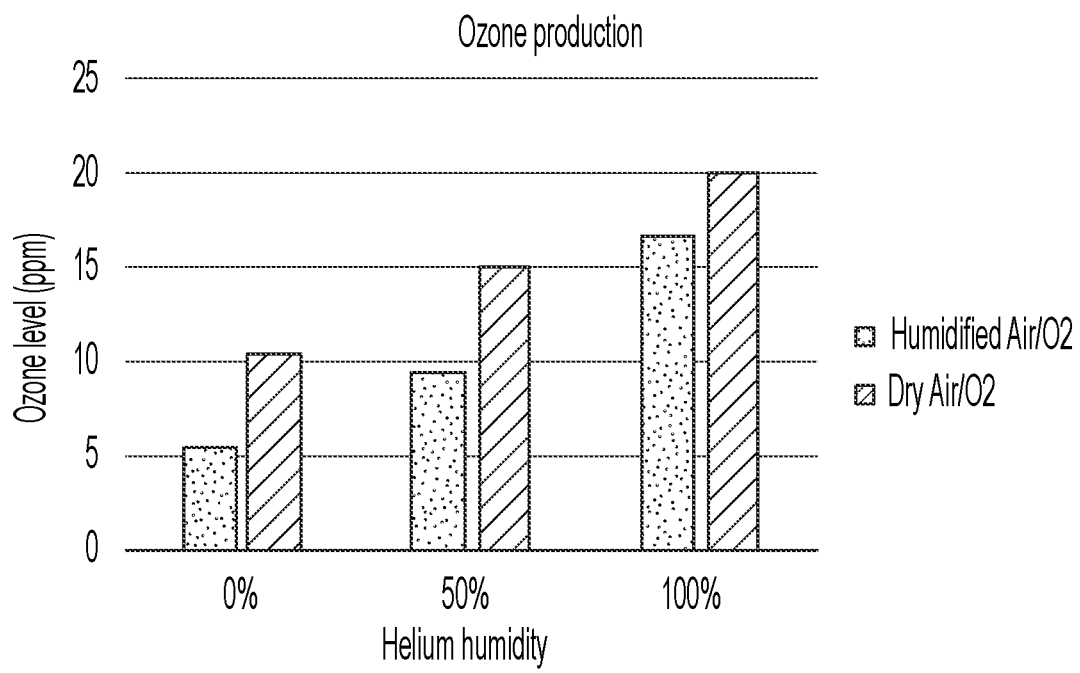
FIG. 14A is a graph of ozone production rate by a system in accordance with a preferred embodiment of the present invention with humidified or dry Air/$O_2$ mixture and He+0-100% humidity.
Figure 14B:
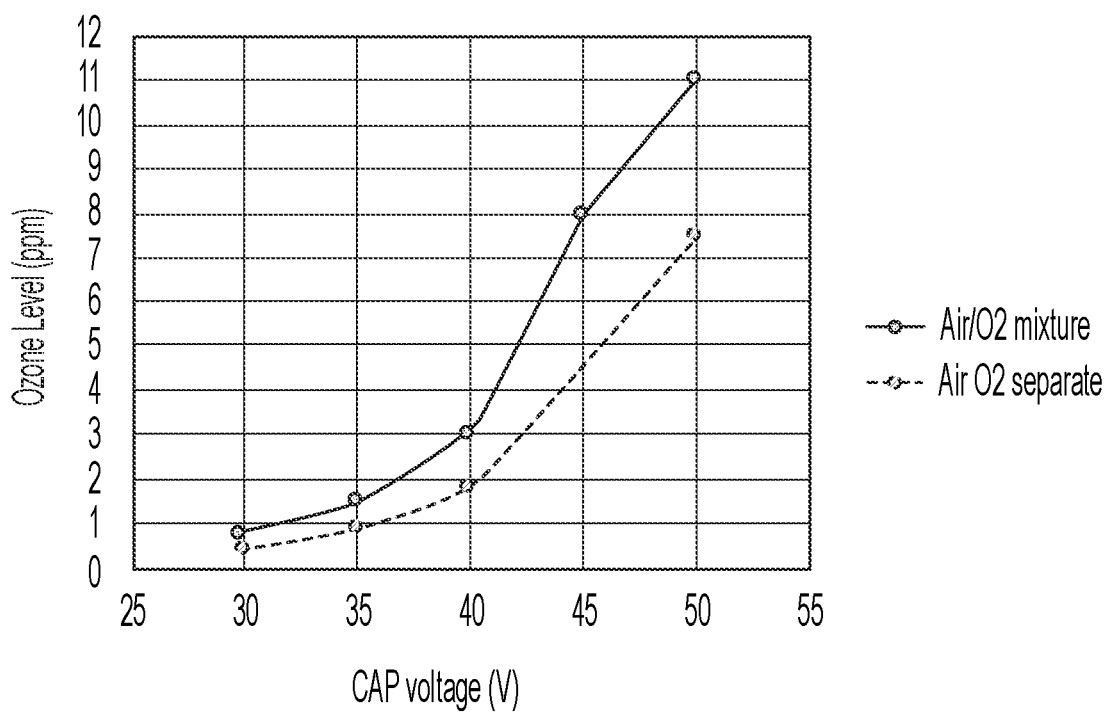
FIG. 14B is a graph of ozone production rate by a system in accordance with a preferred embodiment of the present invention with humidified Air and $O_2$ mixture or separately and humidified He at different voltage.
Figure 14C:
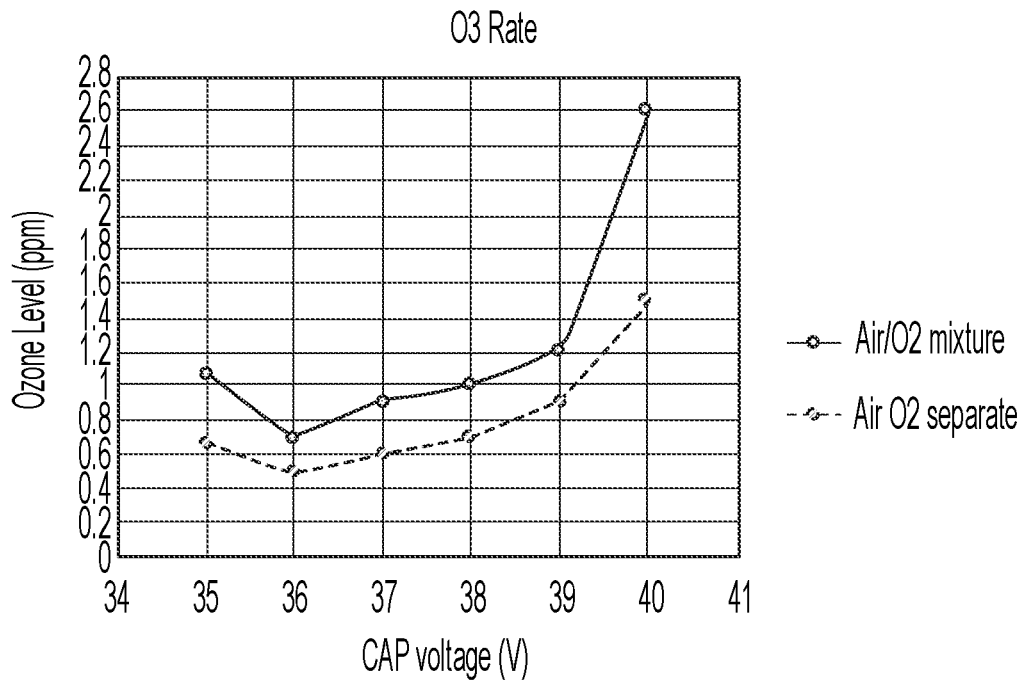
FIG. 14C is a graph of a first set of experimental results of ozone production rate by a system in accordance with a preferred embodiment of the present invention with humidified Air and $O_2$ mixture or separately and humidified He at different voltages ranging from 35-40V.
Figure 14D:
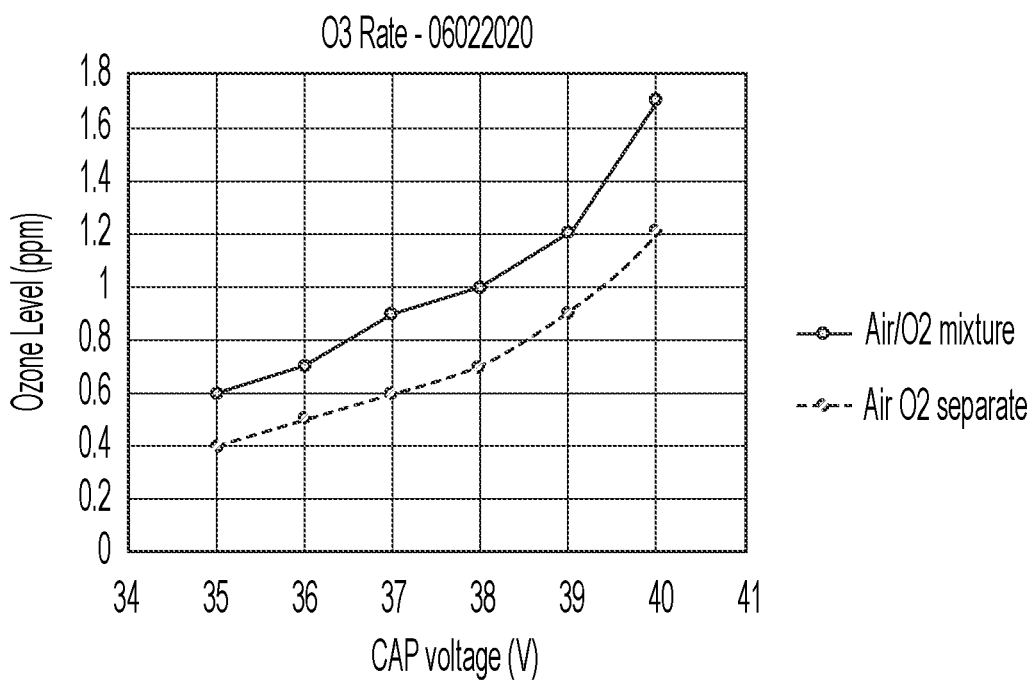
FIG. 14D is a graph a second set of experimental results of ozone production rate by a system in accordance with a preferred embodiment of the present invention with humidified Air and $O_2$ mixture or separately and humidified He at different voltages ranging from 35-40V taken on a different day that the first set.
Figure 15A:
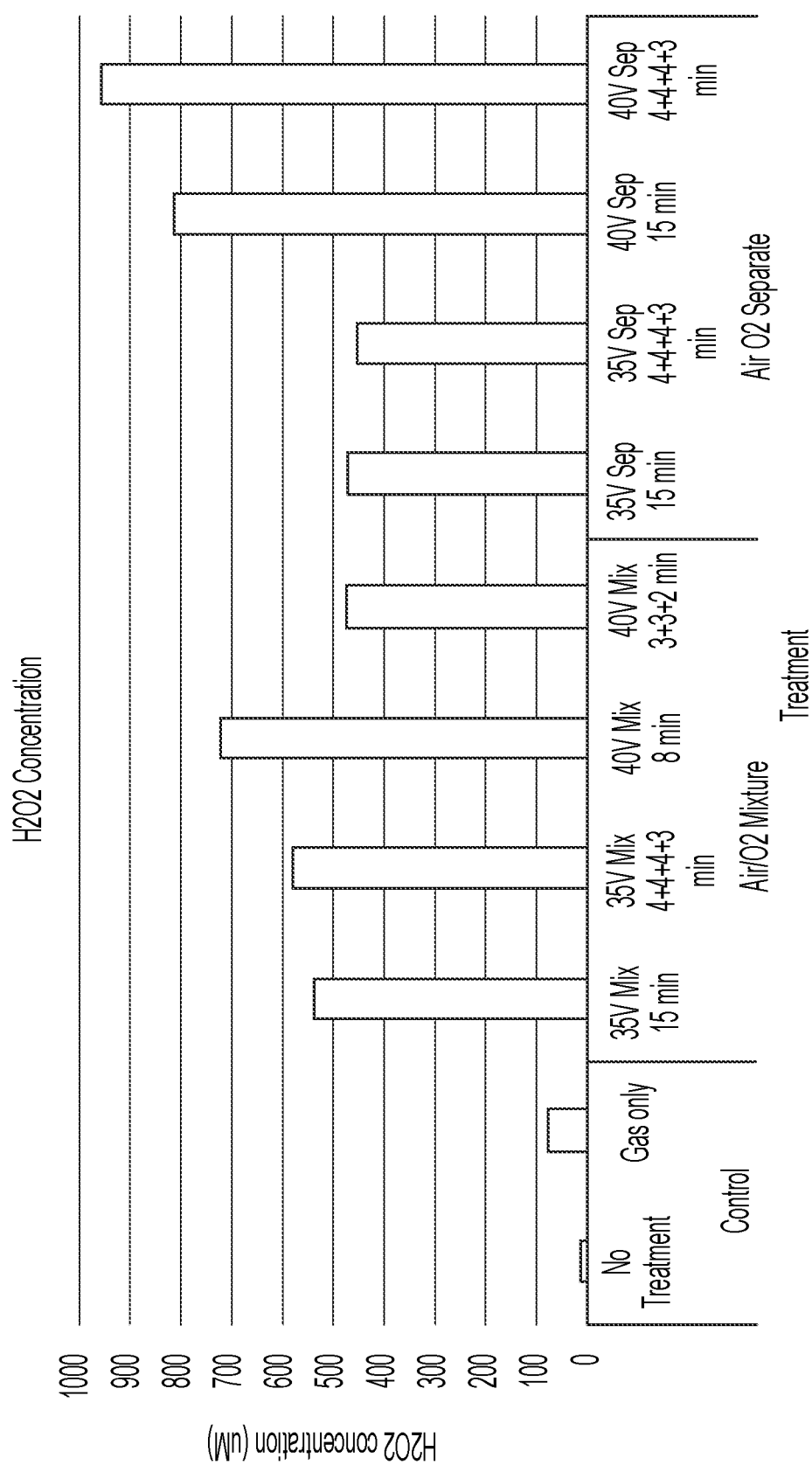
FIG. 15A is a graph of hydrogen peroxide ($H_2O_2$) production rate by a system in accordance with a preferred embodiment of the present invention. PBS was treated with humidified Air/$O_2$ and humidified He with CAP and gas mixture (He, Air and $O_2$) for 8 or 15 min continuously and in intervals.
Figure 15B:
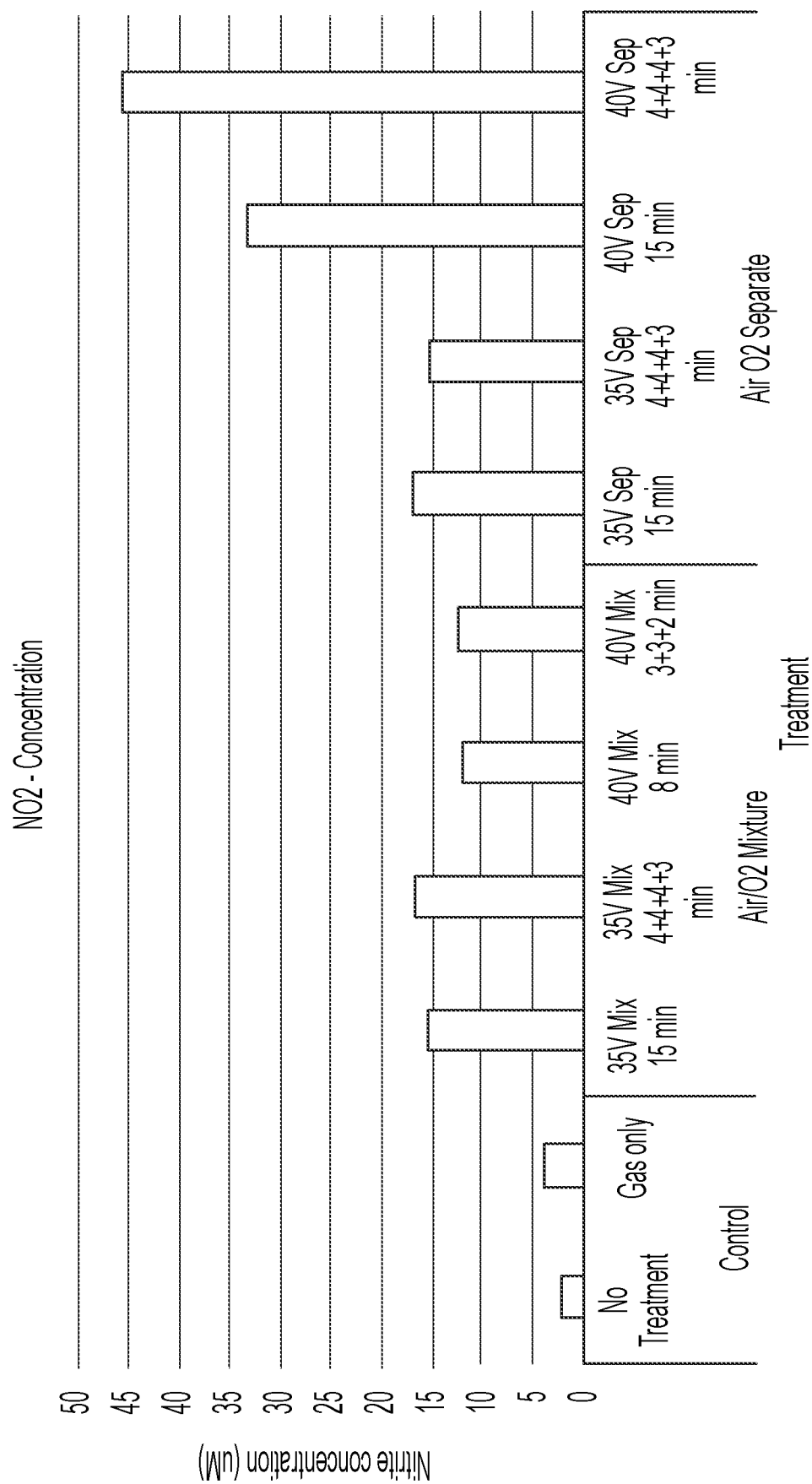
FIG. 15B is a graph of nitrite ($NO_2^-$) production rate by a system in accordance with a preferred embodiment of the present invention. PBS was treated with humidified Air/$O_2$ and humidified He with CAP and gas mixture (He, Air and $O_2$) for 8 or 15 min continuously and in intervals.
Figure 15C:
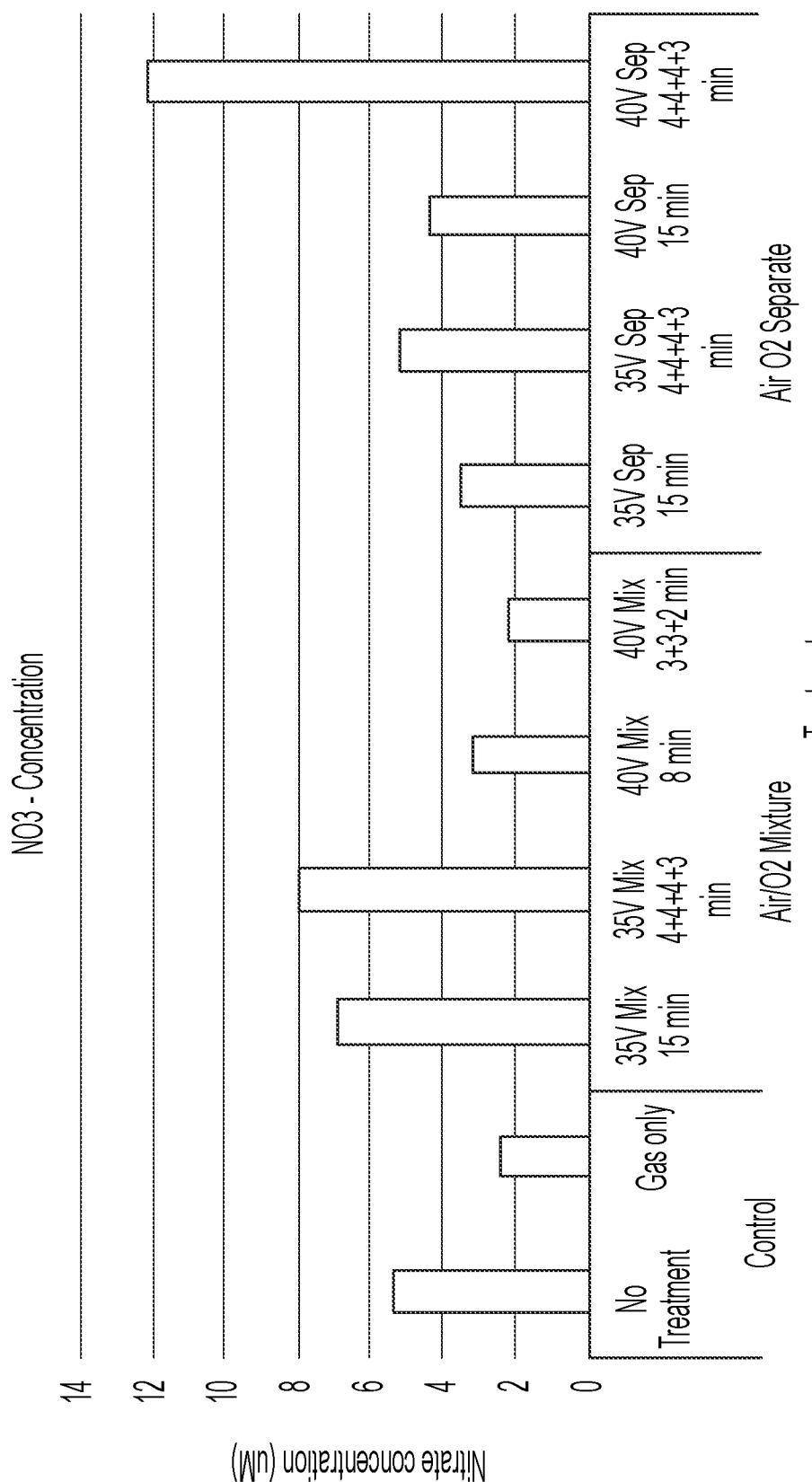
FIG. 15C is a graph of Nitrate ($NO_3^-$) production rate by the by a system in accordance with a preferred embodiment of the present invention. PBS was treated with humidified Air/$O_2$ and humidified He with CAP and gas mixture (He, Air and $O_2$) for 8 or 15 min continuously and in intervals.

The concentrations of $H_2O_2$ and $NO_2^-$ with the present system treatment were plotted in FIGS. 14A and 14B. With CAP turned on, both species are higher when treated in Argon Coag Mode than when treated in Spray Mode. Gas-only treatment was also performed as a control. As indicated in FIGS. 10A and 10B, with 3 min of treatment, Argon Coag Mode at 70 V generated 90 μM $H_2O_2$ and 18 μM $NO_2^-$; whereas Spray Mode at 70 V generated 25 μM $H_2O_2$ and undetectable amount of $NO_2^-$. A gas mixture alone does not generate significant amount of ROS or RNS.

CAP Plasma Ventilator Validation

Cold atmospheric plasma has been reported to induce inactivation of airborne viruses (Xia, T., et al., *Inactivation of airborne viruses using a packed bed non-thermal plasma reactor*. Journal of Physics D: Applied Physics, 2019. 52(25)), deactivation of hepatitis B virus while keeping normal liver function during CAP treatment (Shi, X.-M., et al., *Effect of Low-Temperature Plasma on Deactivation of Hepatitis B Virus*. IEEE Transactions on Plasma Science, 2012. 40(10): p. 2711-2716), inhibition of HIV replication (Volotskova, O., et al., *Cold Atmospheric Plasma Inhibits HIV-1 Replication in Macrophages by Targeting Both the Virus and the Cells*. PLoS One, 2016. 11(10): p. e0165322), inactivation of Newcastle disease virus and avian influenza virus without destruction of the antigenic determinants for vaccine preparation (Wang, G., et al., *Non-thermal plasma for inactivated-vaccine preparation*. Vaccine, 2016. 34(8): p. 1126-32) and so forth. In this study, CAP is combined with a ventilator system to achieve the delivery of CAP as well as the treatment of the virus throughout the patient's respiratory system.

Wu el al (Wu, Y., et al., *MS2 virus inactivation by atmospheric-pressure cold plasma using different gas carriers and power levels*. Appl Environ Microbiol, 2015. 81(3): p. 996-1002) suggested that the ambient air as carrier gas produced the highest level of inactivation at power levels of 20 and 24 W, followed by the gas carriers Ar—$O_2$ (2%, vol/vol) and He—$O_2$ (2%, vol/vol). In addition, air is a required input gas for all ventilators. Hence air as carrier gas is the best option for a CAP-equipped ventilator. Relative humidity (RH) as an important factor of the air will be studied for an optimal configuration in addition to CAP treatment parameters including discharge voltage (V) and treatment time (t).

CAP-Generated Reactive Species

Reactive species generated by CAP can be confirmed within the plasma beam using optical emission spectroscopy (OES) and in aqueous solution by kits based on species.

Reactive Species in the Plasma Beam

An optical emission spectrometer (Ocean Optics HR2000) is used to detect the species in the plasma beam in the range of 200-900 nm. The plasma emissions are collected in a direction perpendicular to the plasma beam axis and at 1-mm increments in axial direction using a collimating lens. The plasma emission is transmitted to the spectrometer via optical fiber.

Reactive Species in the Solution

Kondeti et al did a thorough research on the species generated in CAP-treated saline and water based on their half-lives. Kondeti, V., et al., *Long-lived and short-lived reactive species produced by a cold atmospheric pressure plasma jet for the inactivation of Pseudomonas aeruginosa and Staphylococcus aureus*. Free Radic Biol Med, 2018. 124: p. 275-287. They concluded that long-lived species played a dominant role when the plasma was not in direct contact with the saline; whereas short-lived species was more important when the plasma touched the liquid. Long-lived species in CAP-treated solution like $NO_2^-$ and $H_2O_2$ concentrations can be measured in air flow-treated phosphate buffer saline (PBS) using Griess Reagent System (Promega, G2930) and Fluorimetric Hydrogen Peroxide Assay Kit (Sigma-Aldrich, MAK165-1KT) with CAP on or off. Results will be read by a BioTek microplate reader at 540 nm for absorbance and 540/590 nm for fluorescence, respectively.

Ozone can be a concern for CAP-based ventilator because it can have detrimental impacts on human health. Ozone concentration should be measured at the exhaust of the ventilator and reduced with filters to meet the air quality standards.

CAP Effect on the Cells

Lung cancer cell line A549 will be used for the efficacy of CAP treatment. Air flow-only treatment will be used as control group. The viability of the cells will be evaluated by 3-(4,5-dimethylthiazol-2-yl)-2,5-diphenyl tetrazolium bromide (MTT) assay.

In conclusion, with tuned configuration, CAP-based ventilators could benefit patients with respiratory diseases like pneumonia, COVID19, or lung cancer.

CAP Plasma Virus Inactivation Validation

Respiratory disease-causing viruses such as COVID-19 and severe acute respiratory syndrome (SARS) are transmitted by aerosolized droplets containing the infection virus. Cold atmospheric-pressure plasma (CAP) generates numerous reactive oxygen species (ROS) and reactive nitrogen species (RNS), such as hydrogen peroxide ($H_2O_2$), singlet oxygen ($^1O_2$), ozone (O3), nitric oxide (.NO), and hydroxyl radical (.OH), as well as electrons, ions, and photons, in which .OH, $^1O_2$, .NO, $O_2.-$, $.NO_2$, and ONOO— are short-lived species whereas $H_2O_2$, $NO_2-$, and $NO_3-$, are long-lived species. Various studies have shown that the CAP could inactivate viruses and other microbes. The potential inactivation mechanisms of the virus by the CAP is by inducing to high oxidation-reduction potential (ORP) and electrical conductivity by producing large number of free radicals. The reactive oxygen and nitrogen species could react with carbohydrates and initiate lipid peroxidation and cross-linking of the fatty acid side chains, resulting in alterations of the chemical bonds and molecular structure. They induce oxidative stress by causing protein peroxidation and inducing the destruction of the virus envelope, singlet oxygen could rapidly react with cysteine to generate the major product of cystine (R-cys-S-S-cys-R) with disulfides, they selectively reacted with tyrosine, tryptophan, and histidine to produce hydroperoxides resulting in protein aggregation and ultimately resulting in changes to the viral morphology. Moreover, they can damage viral nucleic acids encoding enzymes, by oxidizing guanine and induce cross-links between guanine and lysine contributing to reduced gene expression and the elimination of virus replication, thereby leading to virus inactivation. The cold plasma system of the present invention generates ionized cold plasma in a humidified setup to produce reactive species that are fed to virus infected patient via endobronchial tube. The output of the system contains reactive o A549 cells were treated with 100% humidified Air/$O_2$ mixture (1:1 v/v) at a flow rate of 2 LPM ($O_2$ fraction 24%). Helium flow rate was 3 LPM and humidity was set at 0%, 50%, and 100%.

A549 cells without treatment attached firmly to the culture dish, and nuclei were intact. The control in this experiment was Air/$O_2$ and He mixture-treated for 10 min. Cells did not demonstrate any morphological changes compared to no treatment.

When He humidity was set at 0% (dry helium), the cells started to shrink within 5 min of cold plasma system treatment, but a significant amount of the cells were still viable. After increasing the treatment time to 10 min, cell death was identified.

When He humidity was increased to 50%, at 5 min of treatment time, the cells demonstrated shrinkage and blebbing of the membrane. Cell shrinkage was more severe at 10 min treatment time, and dead cells were visualized in a floating pattern.

When He humidity was increased to 100% at 5 or 10 min of treatment, almost all the cells were fragmented and not viable.

Figure 10F:
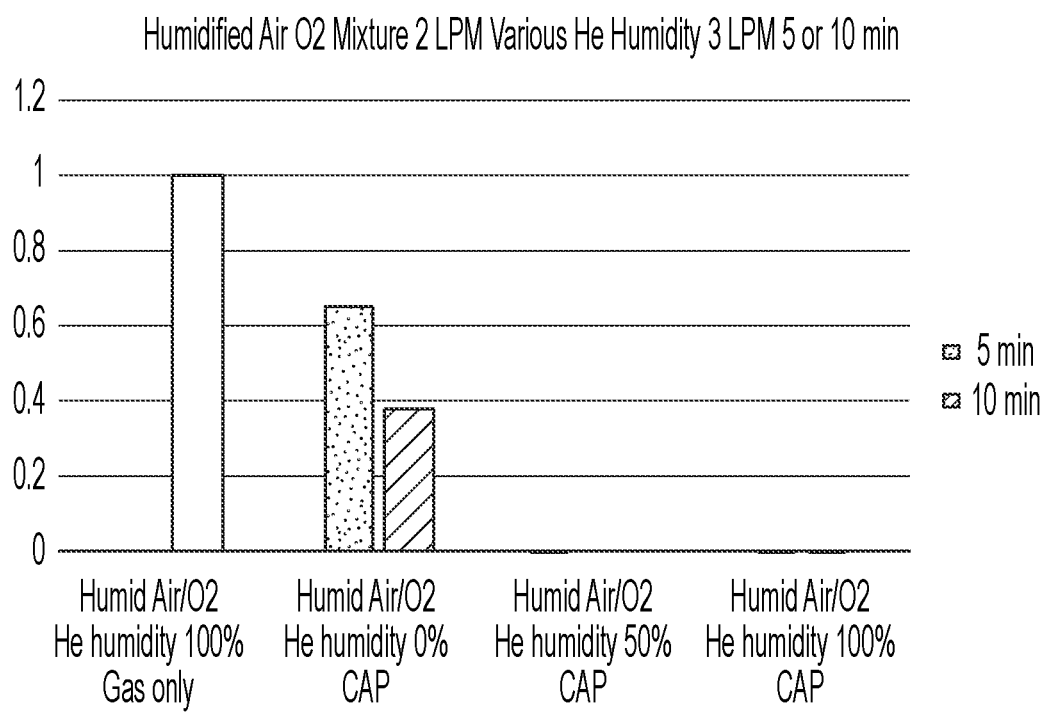
FIG. 10F is a graph of viability of A549 cells treated by a system in accordance with the present invention for 5 or 10 minutes with humidified Air/$O_2$ mixture (with 24% $O_2$) and various helium humidity.

An MTT viability assay was performed on the cells. The results are shown in FIG. 10F. He humidity at 0% (dry helium) and 5 min treatment time reduced the viability to 60%, and at 10 min the viability was reduced the viability to 40% compare to no treatment. When He humidity was set to 50% or 100%, there were no viable cells at 5 or 10 min of treatment.

A more comprehensive study was performed to determine the minimum treatment time required for elimination of A549 cells. A549 cells were treated for 1-5 min with humidified or dry Air/$O_2$ mixture (1:1 v/v) at a flow rate of 2 LPM ($O_2$ fraction 24%). Helium flow rate was 3 LPM and humidity was set at 0%, 50%, and 100%. Images were taken 24 hour-post CAP treatment.

Phase contrast images of the A549 cells treated with a system in accordance with a preferred embodiment of the present invention for 1-5 min with humidified or dry Air/$O_2$ mixture and various humidity of He were taken. When He humidity was set at 0% (dry helium), cell number started to decrease at 5 min of treatment, but cell morphology did not change significantly; when He humidity was set at 50%, cell number started to decrease at 4 min of treatment; when He humidity was set at 100%, cell number started to decrease at 2 min of treatment, and cell membrane and nuclei started to shrink significantly at 4 min of treatment. Humidity of Air/$O_2$ did not induce significant morphological changes.

Figure 10G:
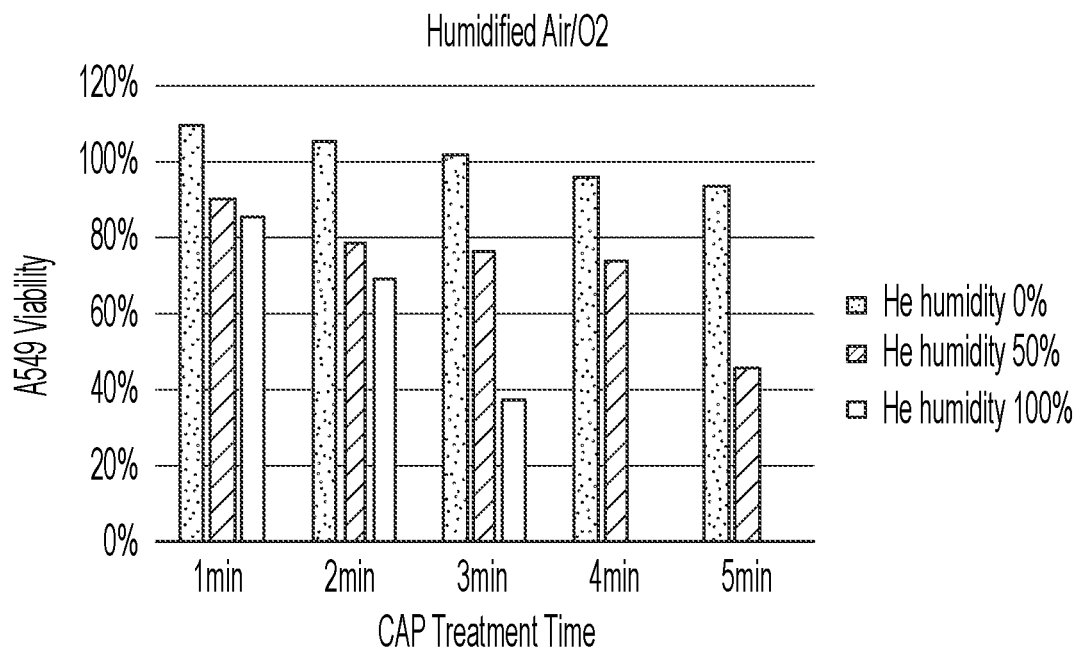
FIG. 10G is a graph of viability of lung cancer cells A549 treated by a system in accordance with a preferred embodiment of the present invention at 48-hour post treatment with humidified Air/$O_2$ mixture and He+0-100% humidity for 1-5 min.
Figure 10H:
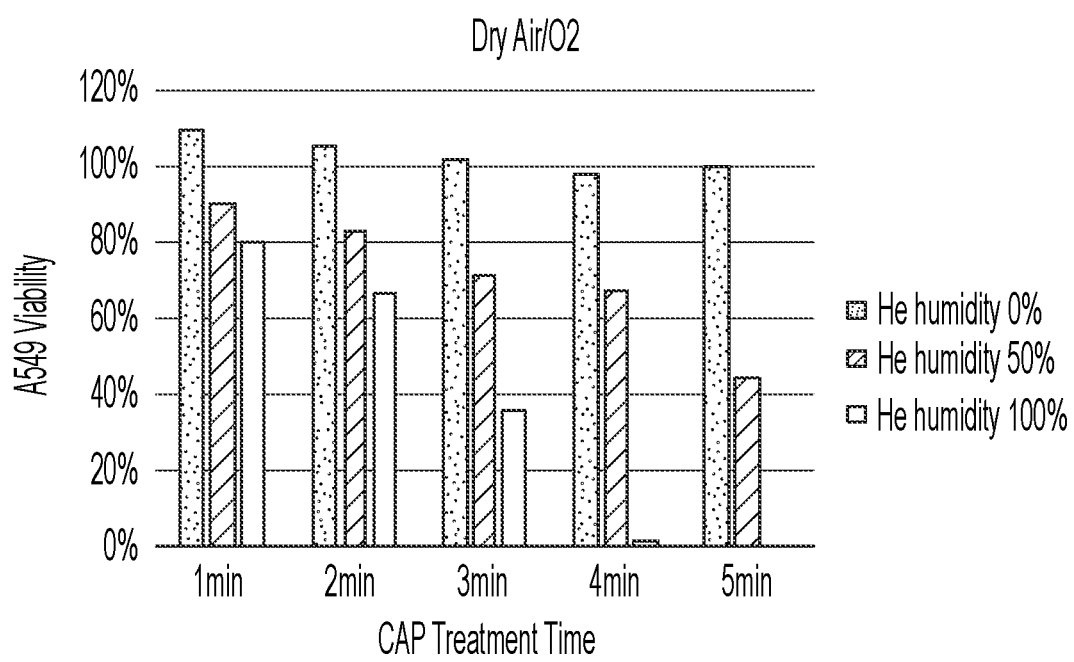
FIG. 10H is a graph of viability of lung cancer cells A549 treated by by a system in accordance with a preferred embodiment of the present invention at 48-hour post treatment with dry Air/$O_2$ mixture and He+0-100% humidity for 1-5 min.

An MTT viability assay was performed on the cells (FIGS. 10G and 10H). He humidity at 0% (dry helium) did not induce much cell death compared to no treatment even at 5 min of treatment. When He humidity was set to 50%, cell viability gradually decreased with increasing of treatment time. About 50% of cells were viable at 5 min of treatment. When He humidity was set to 100%, 3 min of CAP treatment was able to reduce viability to below 50%, and 4 min of treatment completely eliminated the cells. Humidity of Air/$O_2$ did not result in significant differences in viability data. Based on these results, one may conclude that humidification of helium is a critical factor for the cold plasma system to eradicate lung cancer cells.

Separating Oxygen Flow from Air Flow

Figure 11:
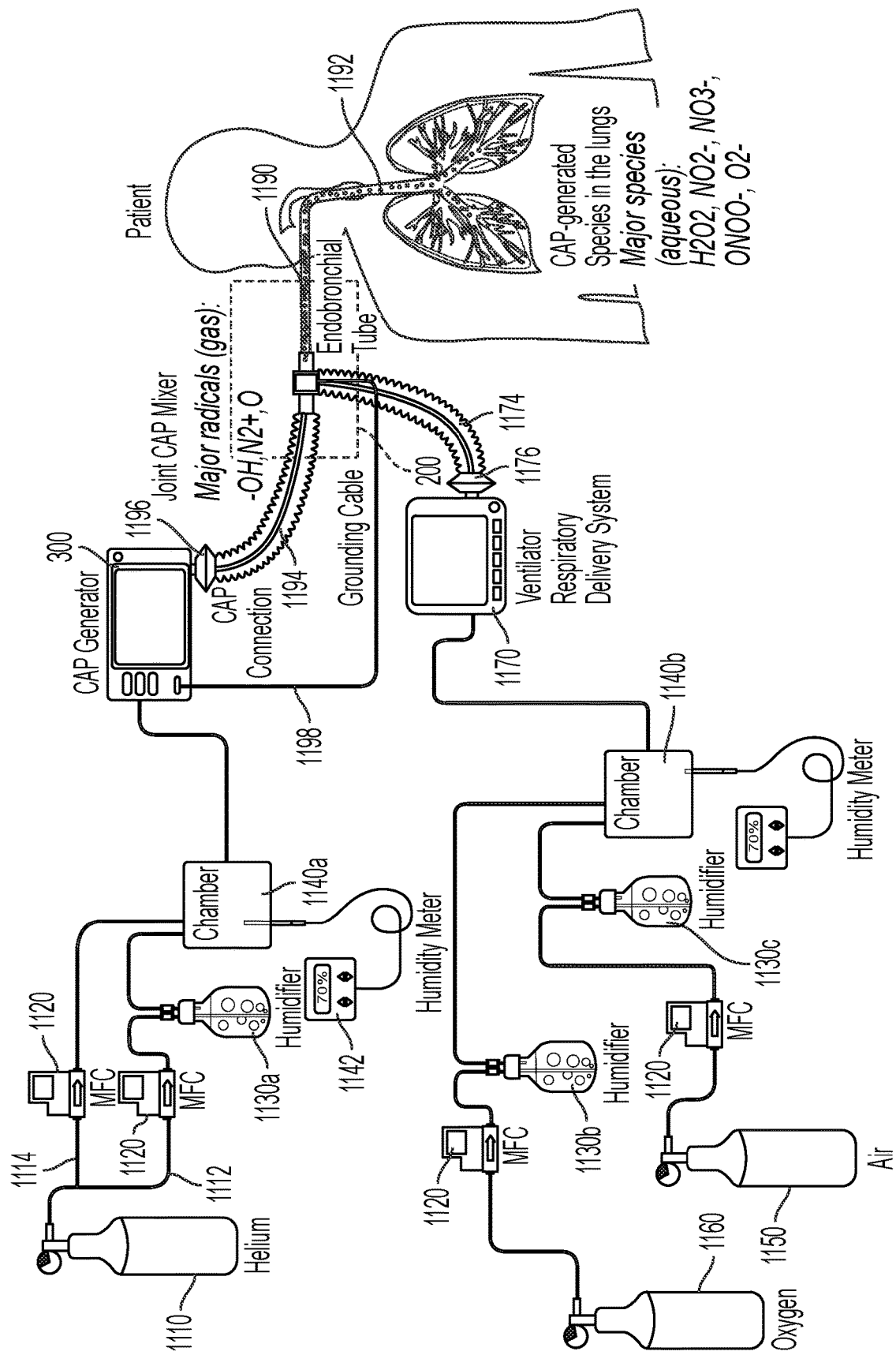
FIG. 11 is a block diagram of a cold atmospheric plasma system having a CAP Joint Mixer for treatment of respiratory infections in accordance with another preferred embodiment in which a carrier gas, a feed gas and a third gas are humidified.
Figure 12:
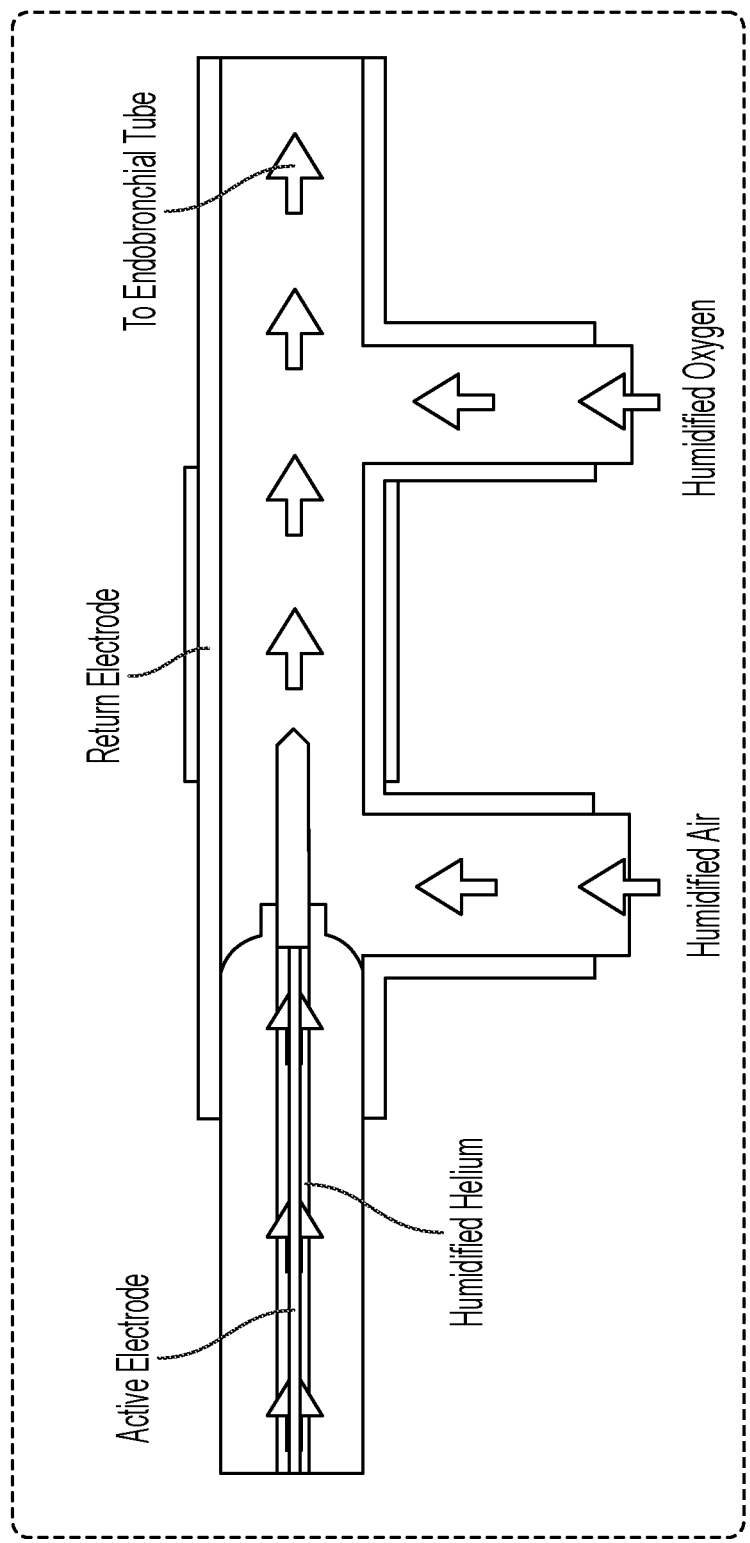
FIG. 12 is a diagram of an alternate embodiment of a CAP Joint Mixer in which supplies of air and oxygen enter the CAP Joint Mixer in different locations such that at least one of the air and oxygen enter the CAP Joint Mixer downstream of the inner electrode.

A cold atmospheric plasma system for treatment of respiratory infections in accordance with a first preferred embodiment of the present invention is described with reference to FIG. 11. A helium gas source 1110 is split into two lines 1112, 1114, with each of the two lines controlled by a mass flow controller (MFC) 1120. The Helium gas flow (50 to 1000 mL/min) in line 1112 is passed through an $H_2O$ filled container (Humidifier 1130a) and then fed into a mixing chamber 1140a. The helium gas flow in the line 1114 is fed directly into the mixing chamber 1140a. In this manner, with the mass flow controllers 1120 on the lines 1112, 1114 a relative $H_2O$ saturation in the gas exiting the chamber 1140a can be adjusted. Adjustment of the gas flow in the two lines 1112, 1114 makes the overall flow rate and humidity fine tuning of the gas flow exiting the chamber 1140a possible. The humidity may be in the range of 20%-100% with a preferred humidity of at least 70%. The total helium flow in this embodiment could be varied from 0.5 L/min to 5 L/min in all cases. The humidity of Helium gas in the chamber 1140a may be measured, for example, via calibrated High-Accuracy Humidity and Temperature Meter (not shown). The humidified helium gas from the chamber 1140a is fed into an electrosurgical generator 300, referred to herein as a "Cold Atmospheric Plasma (CAP) Generator." A variety of electrosurgical generators are known in the art and could be used with the present invention. The gas being fed into the Cold Atmospheric Plasma (CAP) Generator 300 is referred to herein as the "carrier gas."

At the same time, an un-humidified air supply 1150 (feed gas) is controlled by a mass flow controller (MFC) 1120. The air gas flow is passed through a second $H_2O$ filled container (Humidifier 1130b) and then is fed into a mixing chamber 1140b. Also at the same time, a source 1160 of an unhumidified pressurized third gas, oxygen in this case, is connected to a third $H_2O$ filled container (Humidifier 1130c). The humidified third gas (oxygen) is fed into chamber 1140b where it mixes with the humidified air. In this manner, with the mass flow controllers 1120 on the air and oxygen lines the relative oxygen percentage exiting the chamber 1140b can be adjusted. The humidity of each of the air and oxygen may be in the range of 20%-100% with a preferred humidity of at least 70%. The humidity of mixture in the chamber 1140b may be measured, for example, via a calibrated High-Accuracy Humidity and Temperature Meter (not shown) and the oxygen content may be measured for example with an oxygen sensor. The humidified air and oxygen from the chamber 1140b are provided to a respiratory delivery system 1170, such as a ventilator, CPAP machine, BIPAP machine, or other known respiratory deliver system. The respiratory delivery system 1170 will mix, adjust and measure the pressure, flowrate, ratio and frequency of the patient inbreath of exhaust air, oxygen and CO2. The output of the respiratory delivery system 1170 is connected to the CAP joint mixer, for example, via tubing 1174 and connector 1176.

The output of the CAP generator 300 and the respiratory delivery system 1170 are connected to a dielectric barrier discharge (DBD) assembly 200, referred to herein as a "CAP joint mixer." A ground cable 1198 connects an outer electrode of the CAP joint mixer 200 to a ground in the CAP generator 300. While the grounding cable 1198 is shown separate from the tubing 1194 in FIG. 11, other arrangements are possible in which the ground cable 1198 is combined, for example, in a harness with the tubing 1194. Due to the presence of the $H_2O$, the ionization of Helium and $H_2O$ to $He^+ + e^-$ chemical reaction will happen simultaneously. The cold plasma-generated reactive species ($H2O2$, $NO2-$, $NO3-$, $ONOO-$, and $O2-$) are produced.

The output of the CAP joint mixer 200 is connected to a delivery member 1190, which, for example, may be an endobronchial tube, oxygen CPAP (continuous positive airway pressure), BIPAP (Bilevel Positive Airway Pressure), ventilator face mask, or nasal $O_2$ cannula 1190 to deliver reactive species 1192, e.g., H2O2, NO2—, NO3—, ONOO—, and O2-, generated by the system into the patient's respiratory system.

Ozone Measurements

Figure 13A:
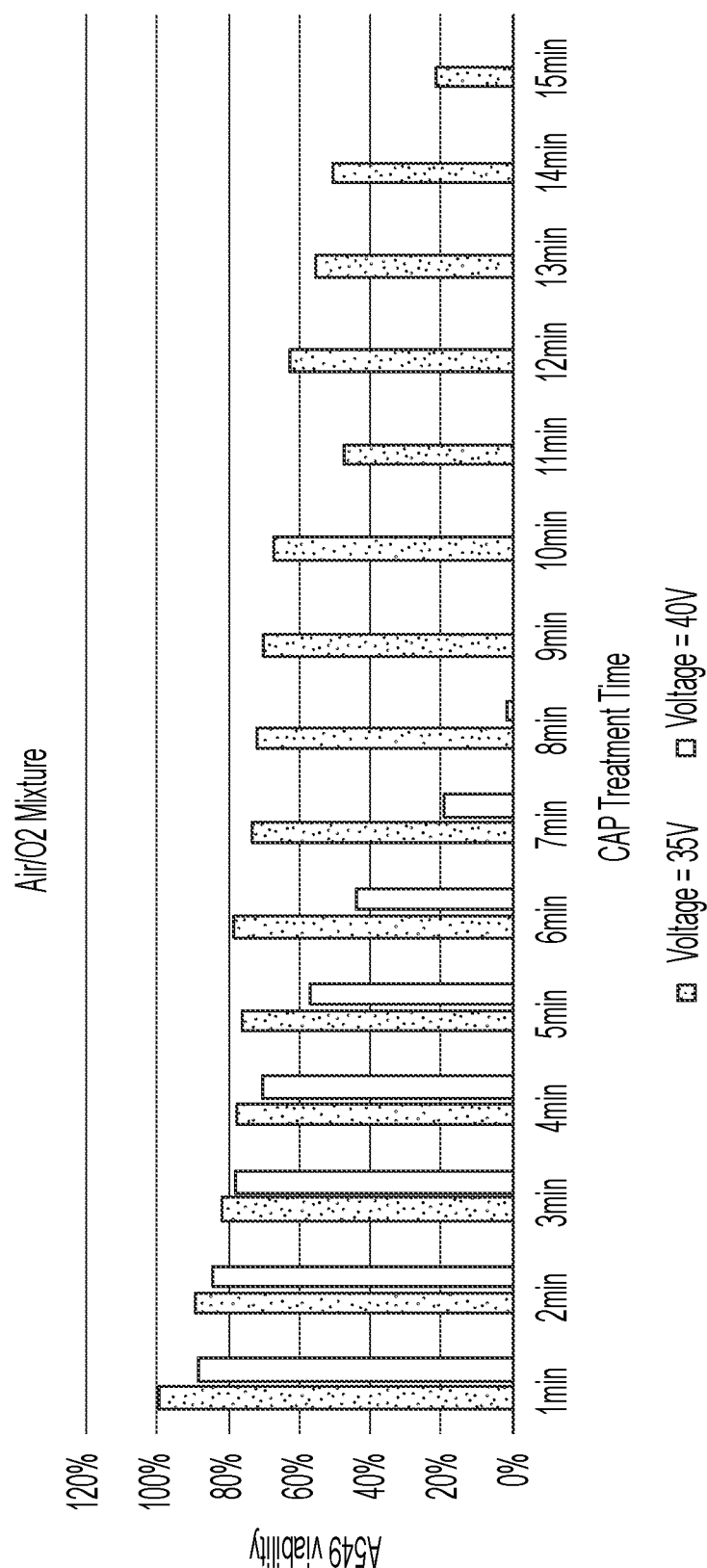
FIG. 13A is a graph of viability of A549 treated by a by a system in accordance with a preferred embodiment of the present invention with humidified Air/$O_2$ mixture.
Figure 13B:
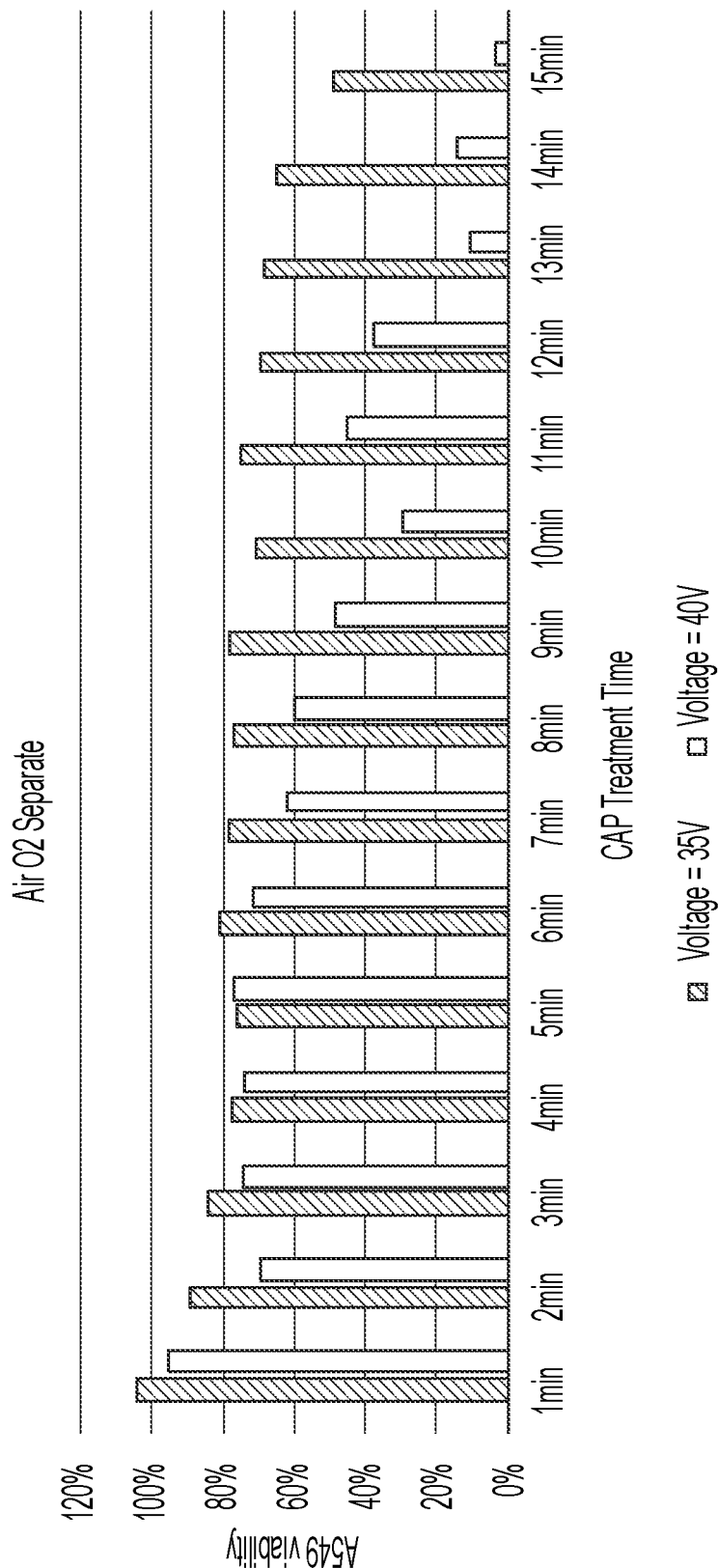
FIG. 13B is a graph of viability of A549 treated by by a system in accordance with a preferred embodiment of the present invention with humidified Air and humidified $O_2$ separately.

Ozone ($O_3$) generated by a system in accordance with a preferred embodiment of the present invention was measured at the end of the endotracheal tube with an ozone detector (Forensics Detectors, Calif.). The measurement was carried out with all settings tested above, i.e., CAP was set to 70 V with humidified or dry Air/$O_2$ mixture (1:1 v/v) at a flow rate of 2 LPM ($O_2$ fraction 24%) and helium flow rate was 3 LPM and humidity was set at 0%, 50%, and 100%. Ozone level was shown in FIG. 14A. At the same helium humidity, dry Air/$O_2$ yielded higher $O_3$ level compared to humidified Air/$O_2$. Higher humidity of helium generated higher concentration of $O_3$, which resulted in stronger reduction effect on the cells as shown earlier in FIGS. 10G and 10H. This correspondence indicates that $O_3$ is a critical species in the cocktail that generated by a system in accordance with a preferred embodiment of the present invention. FIG. 14B shows ozone production rate significantly decreased at lower voltage. Therefore, 35 or 40 V was used to test cell viability instead of 70 V for safety purpose (FIGS. 13A and 13B). $O_3$ production rate was higher when Air and $O_2$ were fed into the system as a mixture (FIG. 14B) compared to separate Air and $O_2$ infusion (FIG. 14B).

However, the cold plasma system with previously demonstrated settings, i.e., CAP was set to 70 V with humidified or dry Air/$O_2$ mixture (1:1 v/v) at a flow rate of 2 LPM ($O_2$ fraction 24%) and helium flow rate was 3 LPM and humidity was set at 0%, 50%, and 100%, produced a large amount of ozone (data demonstrated in Section 2) which is over the safety limit by OSHA standard. In order to lower the ozone generation, lower voltage (35-40 V) was utilized to treat the cells. Because the presence of oxygen in the Air/$O_2$ mixture inflamed the ozone production, Air and $O_2$ were fused into the joint CAP mixer separately to lower the $O_3$ formation. The viability data of A549 cells treated at settings with low $O_3$ level (i.e. lower voltage and separation of Air and $O_2$) is shown in FIGS. 14A and 14B.

When Air and $O_2$ were added to the system as a mixture (FIG. 13A), the capability of CAP on reducing cancer viability was higher compared to where Air and $O_2$ were fused to the system separately (FIG. 13B). CAP treatment of 8 min at 40 V with Air/$O_2$ mixture or 15 min at 40 V with Air and $O_2$ separation were able to lower cancer cell viability to less than 5% percent.

Reactive Species Detection in the Treated Medium

A system in accordance with a preferred embodiment of the present invention was used to treat 1 mL Phosphate Buffer Saline (PBS) in 12-well plates with Argon Coagulation Mode for 8 or 15 min continuously and in intervals. For interval treatment, CAP was administered in 3+3+2 min or 4+4+4+3 min manner with 5 min break between each interval. Voltage was set at 35 or 40 V. Helium, $O_2$ and air were all humidified. Flow rate of helium was set at 3 LPM. Oxygen and air flow rate were both set at 1 LPM.

Among the cocktail plasma-generated reactive oxygen species (ROS) and nitrogen species (RNS) in the treated solution, hydrogen peroxide ($H_2O_2$), nitrite ($NO_2^-$) and nitrate ($NO_3^-$) are the most commonly studied long-lived species. Their concentrations were measured in treated PBS using colorimetric Hydrogen Peroxide Assay Kit (Sigma-Aldrich, MAK311-1KT), Griess Reagent System (Promega G2930) and colorimetric Nitrite/Nitrate Assay Kit (Sigma-Aldrich 23479), with CAP on or off. Results were read by a BioTek microplate reader at 595 nm, 550 nm, and 540/570 nm for absorbance, respectively.

The concentrations of $H_2O_2$, $NO_2^-$ and $NO_3^-$ with a system in accordance with a preferred embodiment of the present invention were plotted. Previous viability data demonstrated that at 40 V, continuous treatment for 8 min with Air and $O_2$ mixture setup or 15 min with Air and $O_2$ separation setup can both lower the viability of A549 to less than 5%. As indicated in FIGS. 15A-15C, 8 min of Air and $O_2$ mixture setup at 40 V generated 725 μM $H_2O_2$, 11.9 μM $NO_2^-$ and 3.3 μM $NO_3^-$, compared to 3+3+2 min interval treatment generated 470 μM $H_2O_2$, 12.5 μM $NO_2^-$ and 2.2 μM $NO_3^-$, whereas continuous 15 min of Air and $O_2$ separation setup at 40 V generated 806 μM $H_2O_2$, 33 μM $NO_2^-$ and 4.3 μM $NO_3^-$ compared to 4+4+4+3 min interval treatment generated 952 μM $H_2O_2$, 45 μM $NO_2^-$ and 12 μM $NO_3^-$. Nitrate ($NO_3^-$) were too low to detect in most of the settings. Gas mixture alone does not generate significant amount of ROS or RNS.

In the case of 8 min continuous treatment, $H_2O_2$ was generated in 1 mL of media by CAP treatment with 5 LPM of gas flow. The detected species were as follows:

$724 \times 10^{-6}$ mol/L×34 g/mol=$24.6 \times 10^{-3}$ mg/mL=24.6 g/m$^3$ of $H_2O_2$ was generated by 40 L of gas mixture;

The $H_2O_2$ level is $24.6 \times 10^{-3}$/ 40=$0.615 \times 10^{-3}$ mg/L=0.615 mg/m$^3$;

In the case of 3+3+2 min interval treatment, the $H_2O_2$ level is 0.4 mg/m$^3$;

In the case of 15 min continuous treatment, the $H_2O_2$ level is 0.365 mg/m$^3$; and In the case of 4+4+4+3 min interval treatment, the $H_2O_2$ level is 0.43 mg/m$^3$.

In all cases, 0.615, 0.4, 0.38, and 0.42 mg/m$^3$ are lower than NIOSH and OSHA permissible exposure limit for $H_2O_2$, which is 1.4 mg/m$^3$ (https://www.cdc.gov/niosh/npg/npgd0335.html).

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A system for performing plasma treatment of respiratory infections comprising:

a source of a carrier gas;

a first humidifier connected to said source of a carrier gas;

a source of a feed gas;

a second humidifier connected to said source of a feed gas;

a plasma generator configured to plasmatize said carrier gas into a plasma;

a mixer having an interior chamber formed from a dielectric, an active electrode inside said interior chamber and connected to an electrical output of said plasma generator, and an outer electrode connected to a ground, wherein said mixer has a first fluid input port connected to said source of a carrier gas and a second fluid input connected to said source of a feed gas; and a fluid delivery member connected to an output of said mixer for delivering reactive species generated in said mixer to a patient.

2. A system for performing plasma treatment of respiratory infections according to claim 1, wherein said carrier gas comprises at least one of helium, argon, nitrogen and oxygen.

3. A system for performing plasma treatment of respiratory infections according to claim 1, wherein said delivery member comprises an endobronchial tube.

4. A system for performing plasma treatment of respiratory infections according to claim 1, wherein said delivery member comprises one of a nasal cannula and a mask.

5. A system for performing plasma treatment according to claim 1, wherein said source of a feed gas comprises one of a ventilator and a continuous positive airway pressure device.

6. A system for performing plasma treatment of respiratory infections according to claim 5, wherein said feed gas comprises a mixture of air and oxygen.

7. A system for performing plasma treatment of respiratory infections according to claim 1, wherein said plasma generator is configured to operate with a frequency in the range of 10 kHz to 200 kHz and an output peak voltage in the range of 3 kV to 6 kV.

8. A system for performing plasma treatment according to claim 1, wherein said plasma generator generates electrical energy having a frequency within 25 kHz of one of 40 kHz, 100 kHz and 200 kHz.

9. A system for performing plasma treatment of respiratory infections according to claim 1, wherein said plasma generator comprises a high frequency electrosurgical generator and a low frequency converter.

10. A system for performing plasma treatment of respiratory infections according to claim 1, wherein said plasma generator comprises:
a power module;
a CPU for controlling said power module;
a memory connected to said CPU; and
a power supply connected to said CPU.

11. A system for performing plasma treatment of respiratory infections according to claim 10, wherein said plasma generator further comprises:
a touchscreen display;
a controller connected to said touchscreen display; and
a graphical user interface configured to display data on said touchscreen display and receive input from a user through said touch-screen display.

12. A system for performing plasma treatment of respiratory infections according to claim 10, wherein said plasma generator further comprises:
a gas module.

13. A system for performing plasma treatment of respiratory infections according to claim 12, wherein said source of a carrier gas is connected to said gas module and said gas module controls a flow of said carrier gas to said mixer.

14. A system for performing plasma treatment of respiratory infections according to claim 13, wherein said first humidifier is connected between said gas module and said mixer.

15. A system for performing plasma treatment of respiratory infections according to claim 13, wherein said first humidifier is connected between said gas module and said source of a carrier gas.

16. A system for performing plasma treatment of respiratory infections according to claim 1, wherein said first humidifier is configured to humidify a carrier gas flowing from said source of a carrier gas to at least 70% humidity and said second humidifier is configured to humidify a feed gas flowing from said source of a feed gas to at least 50% humidity.

17. A system for performing plasma treatment of respiratory infections according to claim 1, wherein said first humidifier is configured to humidify a carrier gas flowing from said source of a carrier gas to 100% humidity and said second humidifier is configured to humidify a feed gas flowing from said source of a feed gas to at least 50% humidity.

18. A system for performing plasma treatment of respiratory infections comprising:
an electrical energy generator configured to generate electrical energy to plasmatize a carrier gas into a plasma; and
a dielectric barrier discharge assembly comprising:
an interior chamber formed from a dielectric, said interior chamber having a first input configured to fluidly connect to a source of a humidified carrier gas, a second input configured to connect to a source of a humidified feed gas, and an output configured to connect to a delivery member;
an active electrode inside said interior chamber and connected to an electrical output of said electrical energy generator; and
an outer electrode connected to a ground;
a first humidifier fluidly connected to said first input of said chamber in said dielectric barrier discharge assembly; and
a second humidifier fluidly connected to said second input of said chamber in said dielectric barrier discharge assembly;
wherein a plasma is generated in said interior chamber when electrical energy is supplied from said electrical energy generator to said interior electrode while both humidified feed gas and humidified carrier gas flow into said interior chamber.

19. A system for performing plasma treatment of respiratory infections according to claim 18, further comprising:
a source of helium connected to an input of said first humidifier; and
a source of air connected to an input of said second humidifier.

* * * * *